US009075225B2

(12) United States Patent
Fine

(10) Patent No.: US 9,075,225 B2
(45) Date of Patent: Jul. 7, 2015

(54) MICROSCOPY IMAGING

(75) Inventor: Alan Marc Fine, Prospect (CA)

(73) Assignee: Alentic Microscience Inc., Halifax, Nova Scotia (CA)

( * ) Notice: Subject to any disclaimer, the term of this patent is extended or adjusted under 35 U.S.C. 154(b) by 496 days.

(21) Appl. No.: 13/095,175

(22) Filed: Apr. 27, 2011

(65) Prior Publication Data

US 2011/0249109 A1 Oct. 13, 2011

Related U.S. Application Data

(63) Continuation-in-part of application No. 12/913,639, filed on Oct. 27, 2010.

(60) Provisional application No. 61/255,781, filed on Oct. 28, 2009.

(51) Int. Cl.

| | |
|---|---|
| ***F16L 5/00*** | (2006.01) |
| ***G02B 21/00*** | (2006.01) |
| ***G01N 21/64*** | (2006.01) |

(52) U.S. Cl.

CPC ........ *G02B 21/0008* (2013.01); *G01N 21/6408* (2013.01); *G01N 21/6458* (2013.01)

(58) Field of Classification Search

CPC ........... G01N 21/6408; G01N 21/6458; G02B 21/0008

USPC ........................................................ 348/79

See application file for complete search history.

(56) References Cited

U.S. PATENT DOCUMENTS

| | | | |
|---|---|---|---|
| 4,338,024 | A | 7/1982 | Bolz et al. |
| 4,612,614 | A | 9/1986 | Deindoerfer et al. |
| 4,882,284 | A | 11/1989 | Kirchanski et al. |
| 4,963,498 | A | 10/1990 | Hillman et al. |
| 5,218,211 | A | 6/1993 | Cresswell et al. |
| 5,307,161 | A | 4/1994 | Miyamoto |
| 5,365,114 | A | 11/1994 | Tsurushima et al. |
| 5,389,779 | A | 2/1995 | Betzig et al. |
| 5,464,752 | A | 11/1995 | Kortright et al. |
| 5,627,041 | A | 5/1997 | Shartle |
| 5,633,972 | A | 5/1997 | Walt et al. |
| 5,653,939 | A | 8/1997 | Hollis et al. |
| 5,739,527 | A | 4/1998 | Hecht et al. |
| 5,851,489 | A | 12/1998 | Wolf et al. |

(Continued)

FOREIGN PATENT DOCUMENTS

| | | | |
|---|---|---|---|
| CN | 102713720 | A | 10/2012 |
| DE | 102011117228 | | 5/2013 |

(Continued)

OTHER PUBLICATIONS

Bayer, Manfred E. and John L. Sloyer, Jr., "The electrophoretic mobility of Gram-negative and Gram-positive bacteria: an electrokinetic analysis", Jan. 31, 1990 (8 pages).

(Continued)

*Primary Examiner* — William C Vaughn, Jr.
*Assistant Examiner* — Naod Belai
(74) *Attorney, Agent, or Firm* — Fish & Richardson P.C.

(57) ABSTRACT

Among other things, an imaging device has a photosensitive array of pixels, and a surface associated with the array is configured to receive a specimen with at least a part of the specimen at a distance from the surface equivalent to less than about half of an average width of the pixels.

18 Claims, 16 Drawing Sheets

631 631 117 129 123 123 119 103 121 2,4 113 2,4 124 124 123 123 107 105 125

(56) References Cited

U.S. PATENT DOCUMENTS 5,880,830 A 3/1999 Schechter
5,894,349 A 4/1999 Harris et al.
5,932,428 A 8/1999 Dubrow et al.
6,083,763 A 7/2000 Balch
6,104,495 A 8/2000 Sieben et al.
6,259,104 B1 7/2001 Baer
6,280,586 B1 8/2001 Wolf et al.
6,297,025 B1 10/2001 Sugihara et al.
6,312,960 B1 11/2001 Balch et al.
6,323,944 B1 11/2001 Xiao
6,387,707 B1 5/2002 Seul et al.
6,396,980 B1 5/2002 Liu et al.
6,432,720 B2 8/2002 Chow
6,506,664 B1 1/2003 Beyne et al.
6,621,079 B1 * 9/2003 Shao et al. .................... 250/306
6,690,464 B1 2/2004 Lewis et al.
6,784,982 B1 8/2004 Blumenfeld et al.
6,803,238 B1 10/2004 Eggers
6,844,150 B2 1/2005 Weiss et al.
6,867,851 B2 3/2005 Blumenfeld et al.
6,901,086 B2 5/2005 Li
7,009,172 B2 3/2006 Publicover et al.
7,023,563 B2 4/2006 Li
7,079,256 B2 7/2006 Li
7,142,571 B2 11/2006 Li
7,151,246 B2 12/2006 Fein et al.
7,153,720 B2 12/2006 Augusto
7,280,222 B2 10/2007 Li
7,310,151 B2 12/2007 Li
7,326,930 B2 2/2008 Crawely
7,385,175 B2 6/2008 Li et al.
7,423,766 B1 9/2008 Li
7,425,460 B2 9/2008 Pain
7,466,409 B2 12/2008 Scherer et al.
7,476,787 B2 1/2009 Thomas et al.
7,518,731 B2 4/2009 Li
7,524,459 B2 4/2009 Adams et al.
7,626,695 B2 12/2009 Betzig et al.
7,651,598 B2 1/2010 Shapiro et al.
7,693,571 B2 4/2010 Arnone et al.
7,719,685 B2 5/2010 Li
7,727,752 B2 6/2010 Klink et al.
7,738,945 B2 6/2010 Fauver et al.
7,751,048 B2 7/2010 Yang et al.
7,773,227 B2 8/2010 Yang et al.
7,792,246 B2 9/2010 Rodenburg et al.
7,796,797 B2 9/2010 Nakaya et al.
7,850,916 B2 12/2010 Wardlaw
7,936,501 B2 5/2011 Smith et al.
7,982,883 B2 7/2011 Cui et al.
7,990,539 B2 8/2011 Li
8,004,692 B2 8/2011 Li
8,027,083 B2 9/2011 Smith et al.
8,089,630 B2 1/2012 Davis et al.
8,120,783 B2 2/2012 Li
8,345,227 B2 1/2013 Zahniser et al.
8,446,667 B2 5/2013 Smith et al.
8,456,633 B2 6/2013 Lewis et al.
8,477,294 B2 7/2013 Zahniser et al.
8,488,111 B2 7/2013 Zahniser et al.
2005/0048498 A1 3/2005 Woudenberg et al.
2005/0190286 A1 9/2005 Kaduchak et al.
2005/0271548 A1 12/2005 Yang et al.
2006/0223165 A1 10/2006 Chang et al.
2006/0263888 A1 11/2006 Fritz et al.
2007/0207061 A1 9/2007 Yang et al.
2007/0258096 A1 11/2007 Cui et al.
2008/0095312 A1 4/2008 Rodenburg et al.
2008/0144899 A1 * 6/2008 Varma et al. .................. 382/129
2008/0259443 A1 10/2008 Smith et al.
2008/0285040 A1 * 11/2008 Fourkas et al. ............... 356/445
2009/0163432 A1 * 6/2009 Takamatsu et al. ............. 514/44
2009/0174936 A1 7/2009 Olszak
2009/0220125 A1 9/2009 Ren et al.
2009/0225319 A1 9/2009 Lee et al.
2009/0233329 A1 9/2009 Rodriguez et al.
2010/0033561 A1 2/2010 Hersee
2010/0067827 A1 3/2010 Ozcan et al.
2010/0097599 A1 4/2010 Lewis et al.
2010/0248300 A1 9/2010 Yoshida et al.
2010/0290049 A1 11/2010 Yang et al.
2010/0296094 A1 11/2010 Yang et al.
2011/0070606 A1 3/2011 Winkelman et al.
2011/0096157 A1 4/2011 Fine et al.
2011/0151502 A1 6/2011 Kendall et al.
2011/0181884 A1 * 7/2011 Cui et al. ...................... 356/436
2011/0211058 A1 9/2011 McCollum et al.
2011/0234757 A1 9/2011 Zheng et al.
2011/0249109 A1 10/2011 Fine
2011/0254533 A1 10/2011 Gong
2012/0223217 A1 9/2012 Zheng et al.
2012/0223291 A1 9/2012 Klem et al.
2013/0002847 A1 1/2013 Zahniser et al.
2014/0002662 A1 1/2014 Lewis et al.
2014/0152801 A1 6/2014 Fine et al.

FOREIGN PATENT DOCUMENTS

EP 1756260 2/2007
EP 2012114 1/2009
EP 2494400 9/2012
JP 4-316478 11/1992
JP 5-219937 8/1993
JP 5243790 9/1993
JP 11-64215 3/1999
JP 2000-146910 5/2000
JP 2002-525587 8/2002
JP 2008-501999 1/2008
JP 05059882 10/2012
JP 2013-509618 3/2013
WO WO00/12123 3/2000
WO WO2005/121749 12/2005
WO WO2008/112416 9/2008
WO WO2009/111573 9/2009
WO WO2009/111577 9/2009
WO WO2011/053631 5/2011

OTHER PUBLICATIONS

Cook, G.M.W., "Glycoproteins in Membranes", Biol. Rev. (1968) 43, pp. 363-391, Jan. 1968 (29 pages).

Kiuchi, Masato and Akiyoshi Chayahara, "Titanium nitride for transparent conductors", Appl. Phys. Left. 64(8), Feb. 21, 1994 (3 pages).

Alpha MED Scientific, Inc., "MED64: A low-noise multi-electrode array system for in vitro extracellular electrophysiology", MED64 product information, www.med64.com, received Jan. 31, 2012 (16 pages).

OmniVision, OV5642, Mar. 21, 2012 http://www.ovt.com/products/sensor.php?id=65, retrieved from Internet on Mar. 21, 2012 (2 pages).

International Preliminary Report on Patentability from corresponding PCT application No. PCT/US2010/054240 mailed May 10, 2012 (7 pages).

International Search Report and Written Opinion from corresponding PCT application No. PCT/US2010/054240 mailed Dec. 27, 2010 (16 pages).

Ji, Honghao, et al., "Contact Imaging: Stimulation and Experiment", IEEE Transactions on Circuits and Systems—I: Regular Papers, vol. 54, No. 8, Aug. 2007 (13 pages).

U.S. Appl. No. 12/913,639 with pending claims.

Zheng, et al., "Supporting Information", SI Text, www.pnas.org/cgi/doi/10.1073/pnas.1110681108, 2011, 3 pages.

Adams ML, Enzelberger M, Quake S, Scherer A. Microfluidic integration on detector arrays for absorption and fluorescence microspectrometers. Sensors and Actuators A: Physical. 2003;104(1):25-31. doi: 10.1016/S0924-4247(02)00477-6.

Adams M, DeRose G, Quake SR, Scherer A. Fundamental approach for optoelectronic and microfluidic integration for miniaturizing spectroscopic devices. . 2002:1-6. doi: 10.1117/12.469818.

Alkaisi MM, Blaikie RJ, McNab SJ, Cheung R, Cumming DRS. Sub-diffraction-limited patterning using evanescent near-field opti-

(56) References Cited

OTHER PUBLICATIONS cal lithography. Appl Phys Lett. 1999;75(22):3560-3562. http://dx.doi.org/10.1063/1.125388. doi: 10.1063/1.125388.

Allier CP, Hiernard G, Poher V, Dimen JM, Bacteria detection with thin wetting film lensless imaging. Biomed Opt Express. 2010;1(3):762-770. doi. 10.136/BOE.1.000762.

Beese L, Feder R, Sayre D. Contact x-ray microscopy. A new technique for imaging cellular fine structure. Biophys J. 1986;49(1):259-268. doi: 10.1016/S0006-3495(86)83639-6.

Beiderman M, Tam T, Fish A, Jullien GA, Yadid-Pecht O. A low-light CMOS contact imager with an emission filter for biosensing applications. Biomedical Circuits and Systems. IEEE Transactions on 2008;2(3):193-203. doi: 10.1109/TBCAS.2008.2001866.

Bishara W, Su T, Coskun AF, Ozcan A. Lensfree on-chip microscopy over a wide field-of-view using pixel super resolution. Opt Express. 2010;18(11):11181-11191. http://www.opticsexpress.org/abstract.cfm?URI=oe-18-11-11181.

Coskun AF, Sencan I, Su T, Ozcan A. Lensless wide-field fluorescent imaging on a chip using compressive decoding of sparse objects. Opt Express. 2010;18(10):10510-10523. http://www.opticsexpress.org/abstract.cfm?URI=oe-18-10-10510.

Cui X, Lee LM, Heng X, et al. Lensless high-resolution on-chip optofluidic microscopes for *Caenorhabditis elegans* and cell imaging. Proceedings of the National Academy of Sciences. 2008. doi: 10.1073/pnas.0804612105.

Ng, Nakagawa T, Mizuno T, et al. Integrated in vivo neural imaging and interface CMOS device: Design, packaging, and implementation. IEEE Sens J. 2008;8(1):121-130. http://pubget.com/paper/pgtmp_3c74d9653c84d6253d0333a781220fb. doi: 10.1109/JSEN.2007.912921.

Daitner Y, Yadid-Pecht O. Low light CMOS contact imager with an integrated poly-acrylic emission filter for fluorescence detection. Sensors (Basel). 2010;10(5):5014-5027. doi: 10.3390/s100505014; 10.3390/s100505014.

Eggers, M. et al, "A Microchip for Quantitative Detection of Molecules Utilizing Luminescent and Radioisotope Reporter Groups", 516 BioFeature, vol. 17, No. 3, 1994 (8 pages).

Faulkner HML, Rodenburg JM. Movable aperture lensless transmission microscopy: A novel phase retrieval algorithm. Phys Rev Lett. 2004,93(2):023903. http://link.aps.org/doi/10.1103/PhysRevLett.93.023903.

Feder R, Costa JL, Chaudahri P, Sayre D. Improved detail in bilogical soft X-ray microscopy: Study of blood platelets. Science. 1981;212(4501):1398-1400.

Fischer UC, Zingsheim HP. Submicroscopic contact imaging with visible light by energy transfer. Applied Physics Letters. 1982;40(3):195-197. doi: 10.1063/1.93050.

Greenbaum A, Luo W, Su TW, et al. Imaging without lenses: Achievements and remaining challenges of wide-field on-chip microscopy. Nat Methods. 2012;9(9):889-895. doi: 10.1038/nmeth.2114; 10.1038/nmeth.2114.

Gurkan U, Moon S, Geckil H, et al. Miniaturized lensless imaging systems for cell and microorganism visualization in point-of-care testing. Biotechnol J. 2011;6(2):138-149. http://europepmc.org/abstract/MED/21298800.

Heng X, Erickson D, Bangh LR, et al. Optofluidic microscopy—a method for implementing a high resolution optical microscope on a chip. Lab Chip. 2006;6(10):1274-1276. http://dx.doi.org/10.1039/B604676B. doi: 10.1039/B604676B.

Heng X, Erickson D, Psaltis D, Yang C. A new imaging method: Optofluidic microscopy. . 2005:60030F-60030F doi: 10.1117/12.632157.

Heng X, Hsiao E, Psaltis D, Yang C. An optical tweezer actuated, nanoaperture-grid based optofluidic microscope implementation method. Opt Express. 2007;15(25):16367-16375. htp://www.opticsexpress.org/abstract.cfm?URI=oe-15-25-16367.

Ji, Hongjao, Abshire PA, Urdaneta M, Smela E. CMOS contact imager for monitoring cultured cells. Circuits and Systems, 2005 ISCAS 2005 IEEE International Symposium on. 2005:3491-3494 vol. 4. doi: 19.1109/ISCAS.2005.1465381.

Ji, Honghao, Sander D, Haas A, Abshire PA. A CMOS contact imager for locating individual cells. Circuits and Systems, 2006 ISCAS 2006 Proceedings 2006 IEEE International Symposium on. 2006:4 pp. doi: 10.1109/ISCAS.2006.1693345.

Ji, Honghao, Sander D, Haas A, Abshire PA. Contact imaging: Simulation and experiment. Circuits and Systems I: Regular Papers, IEEE Transactions on. 2007,54(8):1698-1701.doi. 10.11096/TCSI.2007.902409.

Isikman SO, Bishara W, Mavandadi S, et al. Lens-free optical tomographic microscope with a large imaging volume on a chip. Proceedings of the National Academy of Sciences. 2011. doi: 10.1073/pnas.1015638108.

Isikman SO, Sencan I, Madanyali O, Bishara W, Ozoprak C, Ozcan A. Color and monochrome lensless on-chip imaging of *Caenorhabditis elegans* over a wide field-of-view. Lab Chip 2010;10(9):1109-1112. http://dx.doi.org/10.1039/C001200A. doi: 10.1038/C001200A.

Kobayashi T, Tamura H, Hatanaka Y, et al. Functional neuroimaging by using an implantable CMOS multimodal device in a freely-moving mouse. Biomedical Circuits and Systems Conference (BioCAS), 2011 IEEE. 2011:110-113. doi: 10.1109/BioCAS.2011.6107739.

Lange D, Storment CW, Conley CA, Kovacs GTA. A microfluidic shadow imaging system for the study of the nematode *Caenorhabditis elegans* in space. Sensors Actuators B: Chem. 2005;107(2):904-914. doi:10.1016/j.snb.2004.12.039.

Lee L, Cui X, Yang C, The application of on-chip optofluidic microscopy for imaging *Giardia lamblia* trophozoites and cysts. Biomed Microdevices. 2009;11(5):951-958. http://dx.doi.org/10.1007.s10544-009-9312-x. doi: 10.1007/s10544-009-9312-x.

Lee M, Yaglidere O, Ozean A. Field-portable reflection and transmission microscopy based on lensless holography. Biomed Opt Express. 2011;2(9):2721-2730. doi: 10.1364/BOE.2.002721; 10.1364/BOE.2.002721.

Lee SA, Zheng G, Mukherjee N, Yang C. On-chip continuous monitoring of motile microorganisms on a cPetri platform. Lab Chip. 2012;12(13):2385-2390. doi: 10.1039/c21c40090a; 10.1039/c2lc40090a.

Lorenz KS, Salama P, Dunn KW, Delp EJ. Digital correction of motion artefacts in microscopy image sequence collected from living animals using rigid and nonrigid registration. J Microsc. 2012;245(2):148-160. doi: 10.1111/j.1365-2818.2011.03557.x; 10.1111/j.1365-2818.2011.03557.x.

Maiden AM, Rodeuburg JM. An improved ptychographical phase retrieval algorithm for diffractive imaging. Ultramicroscopy. 2009;109(10):1256-1262. doi: 10.1016/j.ultramic.2009.05.012.

Maiden AM, Rodenburg JM, Humphry MJ. Optical ptychography: A practical implementation with useful resolution. Opt Lett. 2010;35(15):2585-2587. http://ol.osa.org/abstract.cfm?URI=ol-35-15-2585.

Manaresi N, Romani A, Medoro G, et al. A CMOS chip for individual cell manipulation and detection. Solid-State Circuits, IEEE Journal of. 2003;38(12):2297-2305. doi: 10.1109/JSSC.2003.819171.

McCorkle R, Angilello J, Coleman G, Feder R, LA Placa SJ. Flash X-ray microscopy. Science. 1979;205(4404):401-402. doi: 10.1126/science.205.4404.401.

Milanfar P (2010) Super-Resolution Imaging (CRC Press, Boca Raton, FL).

Moon S, Keles HO, Ozcan A, et al. Integrating microfluidics and lensless imaging for point-of-care testing. Biosensors and Bioelectronics. 2009;24(11):3208-3214. doi: 10.1016/j.bios.2009.03.037.

Moscelli N, van den Driesche S, Witarski W, Pastorekova S, Vellekoop MJ. An imaging system for real-time monitoring of adherently grown cells. Sensors and Actuators A: Physical. 2011;172(1):175-180. doi: 10.1016/j.sna.2011.05.010.

Mudanyali O, Tseng D, Oh C, et al. Compact, light-weight and cost-effective microscope based on lensless incoherent holography for telemedicine applications. Lab Chip. 2010;10(11):1417-1428. http://dx.doi.org/10.1039/C000453G. doi: 10.1039/C000453G.

Ng DC, Tokuda T, Nakagawa T, et al. A new neural imaging approach using a CMOS imaging device. Conf Proc IEEE Eng Med Biol Soc. 2006;1:1061-1064. doi: 10.1109/IEMBS.2006.260316.

(56) References Cited

OTHER PUBLICATIONS

Ng DC, Tamura H, Mizuno T, et al. An impmlantable and fully integrated complementary metal-oxide semiconductor device for in vivo neural imaging and electrical interfacing with the mouse hippocampus. Sensors and Actuators A: Physical 2008;145-146(0):176-186. doi: 10.1016/j.sna.2007.11.020.
Ng, D, Tokuda T, Shiosaka S, Tano Y, Ohta J. Implantable microimagers. Sensors. 2008;8(5):3183-3204. http://www.mdpi.com/1424-8220/8/5/3183.
Oh C, Isikman SO, Khadembosseinieh B, Ozcan A. On-chip differential interference contrast microscopy using lensless digital holography. Opt Express 2010;18(5):4717-4726. http://www.opticsexpress.org/abstract.cfm?URI=oe-18-5-4717.
Ohta J, Tagawa A, Minami H, et al. A multimodal sensing device for fluorescence imaging and electrical potential measurement of neural activities in a mouse deep brain. Engineering in Medicine and Biology Society. 2009 EMBC 2009 Annual International Conference of the IEEE. 2009;5887-5890. doi: 10.1109/IEMBS.2009.5334461.
Pang S, Han C, Kato M, Sternberg PW, Yang C. Wide and scalable field-of-view talbot-grid-based fluorescence microscopy. Opt Lett. 2012;37(23):5018-5020. doi: 10.1364/OL.37.005018.
Prakash SB, Nelson NM, Haas AM, et al. BioLabs-on-A-chip: Monitoring cells using CMOS biosensors. Life Science Systems and Applications Workshop, 2006 IEEE/NLM. 2006:1-2. doi: 10.1109/LSSA.2006.250426.
Psaltis D, Quake SR, Yang C. Developing optofluidic technology through the fusion of microfluidics and optics. Nature. 2006;442(7101):381-386. http://dx.doi.org/10.1038/nature05060.
Reale L. Bonfigli F, Lai A, et al. X-ray microscopy of plant cells by using LiF crystal as a detector. Microsc Res Tech. 2008;71(12);839-848. http://europepmc.org/abstract/MED/18785247.
Richard C, Renaudin A, Aimez V, Charette PG. An integrated hybrid interference and absorption filter for fluorescence detection in lab-on-a-chip devices. Lab Chip. 2009;9(10):1371-1376. doi: 10.1039/b819080a; 10.1039/b819080a.
Rodenburg JM, Hurst AC, Cullis AG. Transmission microscopy without lenses for objects of unlimited size. Ultramicroscopy. 2007;107(2-3):227-231. doi: 10.1016/j.ultramic.2006.07.007.
Salama K, Eltoukhy H, Hassibi A, El-Gamal A. Modeling and simulation of luminescence detection platforms. Biosens Bioelectron. 2004;19(11):1377-1386. doi: 10.1016/j.bios.2003.12.031.
Sander D, Dandin M, Hongbao Ji, Nelson N, Abshire P. Low-noise CMOS fluorescence sensor. Circuits and ystems, 2007 ISCAS 2007 IEEE International Symposium on. 2007:2007-2010 doi: 10.1109/ISCAS 2007.378431.
Seo S, Su T, Tseng DK, Erlinger A, Ozcan A. Lensfree holographic imaging for on-chip cytometry and diagnostics. Lab Chip. 2009;9(6):777-787. http://dx.doi.org/10.1039/B813943A. doi: 10.1039/B813943A.
Singh RR, Ho D, Nilchi A, Genov R, Gulak PG. A hybrid thin-film/CMOS fluorescence contact imager. Circuits and Systems, 2009 ISCAS 2009 IEEE International Symposium on. 2009:2437-2440. doi: 10.1109/ISCAS 2009.5118293
Singh RR, Ho D, Nilchi A, Gulak PG, Yau P, Genov R. A CMOS/Thin-film fluorescence contact imaging microsystem for DNA analysis. Circuits and Systems I: Regular Papers, IEEE Transactions on. 2010;57(5):1029-1038. doi: 10.1109/TCSI.2010.2043990.
Singh RR, Leng L, Guenther A, Genov R. A hybrid CMOS-microfluidic contact imaging microsystem. . 2009;739712-739712. doi: 10.1117/12.827862.
Su TW, Seo S, Erlingen A, Ozcan A. High-throughput lensfree imaging and characterization of a heterogeneous cell solution on a chip. Biotechnol. Bioeng. 2009;102(3):856-868. doi: 10.1002/bit.22116; 10.1002/bit.22116.
Tam T, Jullien GA, Yadid-Pecht O. A CMOS contact imager for cell detection in bio-sensing applications. Circuits and Systems, 2007 ISCAS 2007 IEEE International Symposium on. 2007:813-816. doi: 10.1109/ISCAS.2007.378030.
Tokuda T, Ng DC, Yamamoto A, Kagawa K, Nunoshita M, Ohta J. A CMOS optical/potential image sensor with 7.5 μm pixel size for on-chip neural and DNA spot sensing. Engineering in Medicine and Biology Society, 2005 IEEE-EMBS 2005 27th Annual International Conference of the. 2005;7269-7272. doi: 10.1109/IEMBS.2005.1616189.
Tseng D, Mudanyali O, Oztoprak C, et al. Lensfree microscopy on a cellphone. Lab Chip. 2010; 10(14):1787-1792. http://dx.doi.org/10.1039/C003477K. doi: 10.1039/C003477K.
Wang A, Gill O, Molnar A. Light field image sensors based on the talbot effect. Appl Opt. 2009;48(31):5897-5905. http://ao.osa.org/abstract.cfm?URI=ao-48-31-5897.
Zheng G, Lee SA, Yang S, Yang C. Sub-pixel resolving optofluidic microscope for on-chip cell imaging. Lab Chip. 2010;10(22):3125-3129 http://dx.doi.org/10.1039/C0LC00213E. doi: 10.1039/C0KC00213E.
Zheng G, Cui X, Yang C. Surface-wave-enabled Darkfield aperture for background suppression during weak signal detection. Proceedings of the National Academy of Sciences. 2010. doi: 10.1073/pnas.0912563107.
Zheng G, Lee SA, Antebi Y, Elowitz MB, Yang C. The ePetri dish, an on-chip cell imaging platform based on subpixel perspective sweeping microscopy (SPSM). Proceedings of the National Academy of Sciences. 2011. doi: 10.1073/pnas.1110681108.
Voluntary amendment filed with English translation of Chinese Application No. 201080059753.X filed Feb. 7, 2013 (17 pages).
Office action with English translation from Chinese Application No. 20108005975.X issued Dec. 25, 2013 (19 pages).
Response to European Communication dated Jun. 5, 2012 in European application No. 10827423.4, filed Dec. 10, 2012 (15 pages).
U.S. Appl. No. 12/913,639.
Lee, Seung Ah, et al., "Supplementary Information for: Sub-pixel resolving optofluidic microscope for on-hip cell imaging", Supplementary Material (ESI) for Lab on a Chip, The Royal Society of Chemistry, 2012 (4 pages).
Baranov, A.E. et al., "Use of Blood Cell Count Changes after Radiation Exposure in Dose Assessment and Evaluation of Bone Marrow Function", Institute of Biophysics, Ministry of the USSR, Moscow, USSR, 1990 (17 pages).
Response to Office action with English translation from Chinese Application No. 201080059753.X filed Jul. 9, 2014 (11 pages).
Office action with English translation issued Apr. 2, 2014 in Japanese application 2012-536989 (12 pages).
Entcheva, Emilia, et al., "Contact Fluorescence Imaging of Reentry in Monolayers of Cultured Neonatal Rat Ventricular Myocytes", Department of Biomedical Engineering, The Johns Hopkins University School of Medicine, Baltimore, Maryland, Journal of Cardiovascular Electrophysiology, vol. 11, No. 6, pp. 665-676, Jun. 2000 (13 pages).
Entcheva, Emilia, et al. "Fluorescence Imaging of Electrical Activity in Cardia Cells Using an All-Solid-State System", IEEE Transactions on Biomedical Engineering, vol. 51, No. 2, pp. 333-341, Feb. 2004 (9 pages).
Entcheva, Emilia, et al, "Macroscopic optical mapping of excitation in cardiac cell networks with ultra-high spatiotemporal resolution", Progress in Biophysics & Molecular Biology, vol. 92, pp. 232-257, 2006 (26 pages).
Liu, Yingkai, et al., "Cell-lab on a chip: a CMOS-Based Microsystem for Culturing and Monitoring Cells", Proceedings of the 26$^{th}$ Annual International Conference of the IEEE EMBS, San Francisco, CA, pp. 2534-2537, Sep. 1-5, 2004 (4 pages).
Lu, Steven N., et al., "Optical Mapping of Anatomical Reentry in Monolayers of Cultured Neonatal Rat Cardiac Myocytes", Proceedings of the First Joint BMES/EMBS Conference, Serving Humanity, Advancing Technology, Oct. 13-16, 1999 (1 page).
Ng, David, et al., "Integrated In Vivo Neural Imaging and Interface CMOS Devices: Design, Packaging, and Implementation", IEEE Sensors Journal, vol. 8, No. 1, pp. 121-130, Jan. 2008 (10 pages).
Barda Broad Agency Announcement for the Addvanced Research and Development of Chemical, Biological, Radiological, and Nuclear Medical Countermeasures, "Development of a Rapid, Point-of-Care Biodosimeter to Determine Absorbed Radiation Dose", White Paper for Research Areas 6.1 and 6.2 (Biodosimetry Diagnostics), Jun. 7, 2013 (13 pages).

(56) References Cited

OTHER PUBLICATIONS

Zheng, Guoan, et al., "Scanning Projective Microscopy for 2D and 3D imaging", Electrical Engineering, California Institute of Technology, 2011 (5 pages).
Bayer, Manfred, et al., "The electrophoretic mobility of Gram-negative and Gram-positive bacteria: an eletrokinetic analysis", Jan. 31, 1990 (8 pages).
Cook, G.M.W., "Glycoproteins in Membranes" Biol. Review, vol. 43, pp. 363-391, 1968 (29 pages).
MED64, "A low-noise multi-electrode array system for in vitro extracellular electrophysiology", Alpha MED Scientific Inc., 2010 (16 pages).
Kiuchi, Masato, et al., "Titanium nitride for transparent conductors", Applied Physics Letters, 1994 (3 pages).
Rojas-Palma, Carlos, "Triage, Monitoring and Treatment Handbook," 2009 (290 pages).
PCT application No. PCT/JP2007/000401 filed Apr. 26, 2006 (22 pages).
Optofluidics, "Optofluidic microscope shrinks to fit on a chip", optics.org/ole, Oct. 2008 (2 pages).
Sadrozinski, Harmut F, et al., "The Particl Tracking Silicon Microscope PTSM", Nov. 15, 2003 (5 pages).
Cabello, Jorge, et al., "Digital autoradiography using room temperature CCD and CMOS imaging technology", Phys. Med. Biol. 52 (2007), 4993-5011 (19 pages).
Final Office action dated Jun. 6, 2014 (14 pages).
Waselenko, Jamie K., "Medical Management of the Acute Radiation Syndrome: Recommendations of the Strategic National Stockpile Radiation Working Group", Annual Internal Medicine, 2004 (19 pages).
American Red Cross, "Planning Guidance for Response to a Nuclear Detonation", Jun. 2010 (135 pages).
Nakayama, Yasuhiro, "Varied Effects of Thoracic Irradiation on Peripheral Lymphocyte Subsets in Lung Cancer Patients", Internal Medicine vol. 34, No. 10, Oct. 1995 (7 pages).
Goans, Ronald E., et al., "Early Dose Assessment in Criticality Accidents", Health Physics Society, 2001 (4 pages).
Goans, Ronald E., et al., "Early Dose Assessment Following Severe Radiation Accidents", Health Physics, 72(4):513-518, Apr. 1997, abstract (1 page).
Baranov, AE., et al., "Chernobyl experience: biological indictors of exposure to ionizing radiation", Stem Cells, 13 Suppl 1:69-77, May 1995 (2 pages).
Koenig, Kristi L., et al., "Medical Treatment of Radiological Casualties: Current Concepts", Disaster and Terrorism/Review Article, Jan. 20, 2005 (10 pages).
Williams, Jacqueline P., "Animal Models for Medical Countermeasures to Radiation Exposure", National Institute of Health, Apr. 2010 (35 pages).
Ivashkevich, Alesia N. et al., "γH2AX foci as a measure of DNA damage: A computational approach to automatic analysis", Mutation Research 711, 49-60, 2011 (12 pages).
Farsiu, Sina, et al., "Multiframe Demosaicing and Super-Resolution of Color Images", IEEE Transactions on Image Processing, vol. 15, No. 1, Jan. 2006 (19 pages).
Vaurijoux, Aurelie, et al., "Biological Dosimetry of Ionizing Radiation", Laboratory of Biological Dosimetry, www.intechopen.com, Feb. 12, 2012 (21 pages).
Swartz, Harold, M., et al., "A Critical Assessment of Biodosimetry Methods for Large-Scale Incidents", vol. 98, No. 2, Feb. 2010 (14 pages).
Alexander, George A., et al., "BiodosEPR-2006 Meeting: Acute dosimetry consensus committee recommendations on biodosimetry applications in events involving uses of radiation by terrorists and radiation accidents", Science Direct, 2007 (25 pages).
Seo, Sungkyu, et al., "High-Throughput Lens-Free Blood Analysis on a Chip", Anal. Chem. 82, 4621-4627, 2010 (7 pages).
Mundanyali, Onur, et al., "Lenless On-Chip Imaging of Cells provides a new tool for high-throughout cell-biology and medical diagnostics", Journal of Visualized Experiments, 2009 (3 pages).
Webster, J.R., et al., "Monolithic Electrophoresis Device with Integrated Fluorescence Detector", Anal. Chem. 1622-1626, 2001 (5 pages).
Mundayali, Onur, et al., "Compact, light-weight and cost-effective microscope based on lensless incoherent holography for telemedicine applications", Lab on a Chip, 2010 (20 pages).
International Search Report and Written Opinion mailed Jul. 17, 2014 from corresponding PCT Application No. PCT/CA2014/050070 (4 pages).
Transaction history and pending claims from U.S. Appl. No. 12/913,639 as of Aug. 13, 2014.
Transaction history and pending claims from U.S. Appl. No. 14/173,500 as of Aug. 13, 2014.
Decision of Rejection with English translation from Japanese application 2012-536989 issued on Mar. 2, 2015 (11 pages).

* cited by examiner

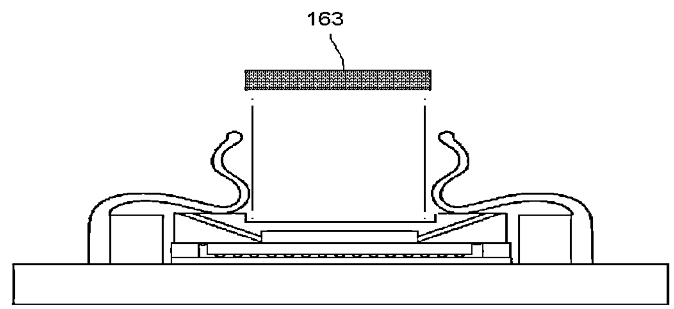
FIG. 5A
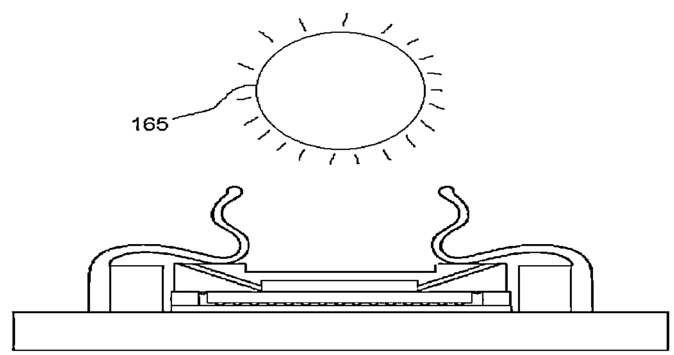
FIG. 5B
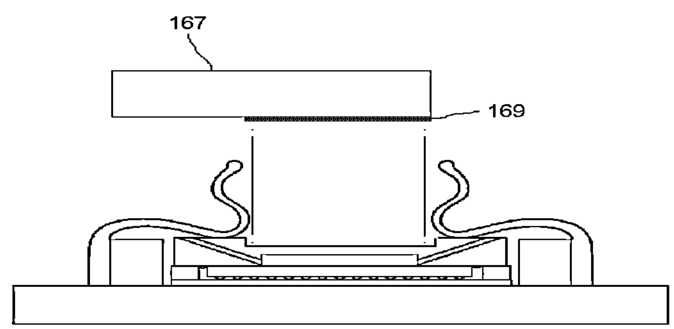
FIG. 5C
FIGURE 5

MICROSCOPY IMAGING

This application is a continuation-in-part of U.S. patent application Ser. No. 12/913,639, filed Oct. 27, 2010, which is entitled to the benefit of the filing date of U.S. provisional application Ser. 61/255,781, filed Oct. 28, 2009, both of which are incorporated by reference here in their entirety.

BACKGROUND

Microscopy in its various forms is an essential tool in an ever-growing range of human activity, from basic research in the natural sciences, industrial research and development, process and quality control, forensics and biosafety, to clinical human and veterinary medical diagnostics, among others. The most widely used form of microscopy is optical. The resolution of standard forms of optical microscopy, however, is limited to several hundred nanometers by the diffraction of light between the specimen and the microscope objective lens. Due to its wave properties, light passing through a circular lens creates a ring-shaped diffraction pattern; the images of two different points formed by such a lens can be resolved if the principal diffraction maximum of one point lies outside of the first minimum of the other point. This theoretical diffraction limit, also known as the Abbe limit or Rayleigh criterion, is approximately equal to $0.61\lambda/NA$, where $\lambda$ is the wavelength of the light and NA is the numerical aperture of the lens, given by $$NA=n \sin \alpha$$

where n is the index of refraction of the optical medium between the lens and the specimen and $\alpha$ is the half-angle of acceptance of the lens. Currently available microscope objective lenses typically have NA<1.4, so that the theoretical diffraction limit for visible light is >200 nm; in practice the resolution limit of standard optical microscopes, compromised by various lens aberrations, is poorer, seldom much below 0.5 μm.

A variety of approaches have been taken to reduce or overcome the diffraction limit. NA can be increased by use of high refractive index media. The size of an illumination spot can be reduced by strategies such as stimulated emission depletion (STED), or the positions of sparse individual molecules can be approximated by the centers of their diffracted images.

Near-field scanning optical microscopes (NSOMs) can overcome the diffraction limit by using a probe having a tip smaller than the wavelength of light and positioned less than a wavelength from the specimen. In a typical configuration, the probe tip or aperture is scanned along the specimen close to its surface to map the near field produced by fluorescence at the specimen surface. NSOM imaging is non-destructive and can be carried out in an aqueous environment, permitting observation of living cells and hydrated molecules.

Other methods exist that do not require scanning, but instead require a superlens. Lensless microscopy methods are known, however they may require integration of multiple images or subsequent computational image derivation in order to produce usable images.

SUMMARY

In general, in an aspect, an imaging device has a photosensitive array of pixels, and a surface associated with the array is configured to receive a specimen with at least a part of the specimen at a distance from the surface equivalent to less than about half of an average width of the pixels.

Implementations may include one or more of the following features. A specimen chamber adjacent the surface is defined in part by a wall that is spaced apart from the surface and transmits light to illuminate the specimen. A fluid channel carries a fluid specimen into the chamber. A second fluid channel carries the fluid specimen out of the chamber.

The array of the imaging device is positioned near an atomic force microscope. The chamber lid has one or more electrodes contacting the top of the specimen chamber. The surface of the photosensitive array has a conductive layer functioning as one or more surface electrodes. The one or more surface electrode(s) and the chamber lid electrode(s) are connected by wires to a potential-applying or potential-measuring device. The chamber lid electrodes are arranged in a matrix. The surface electrodes are arranged in a matrix. The potential-applying device is configured to address each chamber lid electrode and/or surface electrode individually or as a group. The imaging device is used for fluorescence lifetime imaging. The light source emits light primarily in the far ultraviolet wavelength band. The imaging device is used to collect specimen at the surface of the imaging device or at the top of the specimen chamber. The imaging device is used to perform wound healing experiments. The imaging device is used to perform cell migration experiments.

Among other advantages of these and other aspects and features are the following. These approaches in devices are simple, easy to use, not cumbersome, have broad applicability to a very wide range of applications, are relatively inexpensive and rapid. In some implementations, they are suitable for imaging of moving or rapidly changing specimens. Difficult to fabricate and/or expensive optical elements may not be required.

These and other features and aspects, and combinations of them, may be expressed as methods, systems, components, means and steps for performing functions, business methods, program products, and in other ways.

Other advantages and features will become apparent from the following description and from the claims.

DESCRIPTION

FIGS. 5A, 5B, and 5C show section views of an imaging device with light sources: light-emitting diodes (FIG. 5A), ambient (FIG. 5B), and portable multi-color (FIG. 5C).

Figure 1:
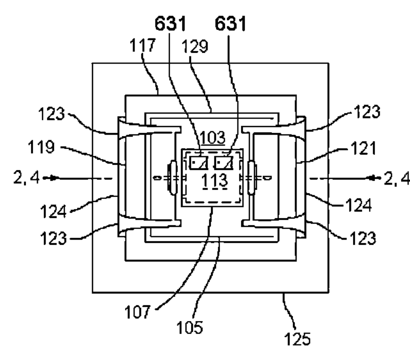
FIG. 1 shows a top view of an imaging device.
Figure 2:
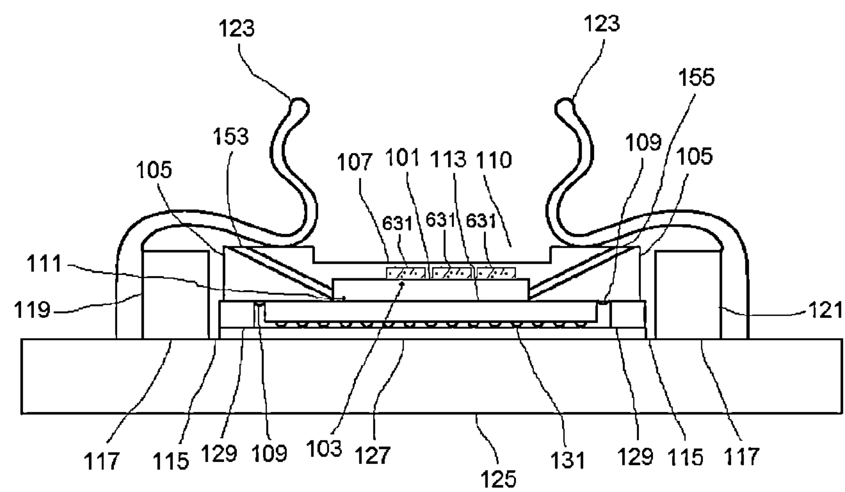
FIG. 2 shows a section view of an imaging device.
Figure 3:
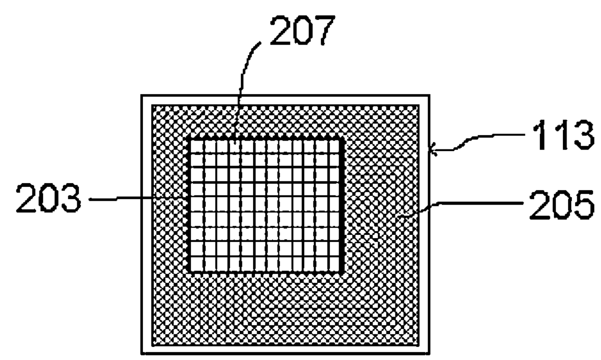
FIG. 3 shows a top view of an imaging integrated circuit.
Figure 4:
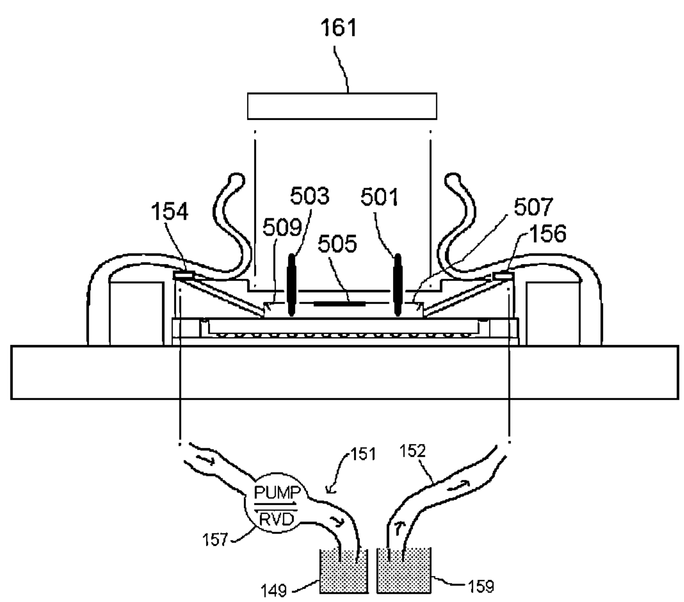
FIG. 4 shows a section view of an imaging device equipped with a light source, a probe, electrodes, a heating element, and a fluid flow system.
Figure 6:
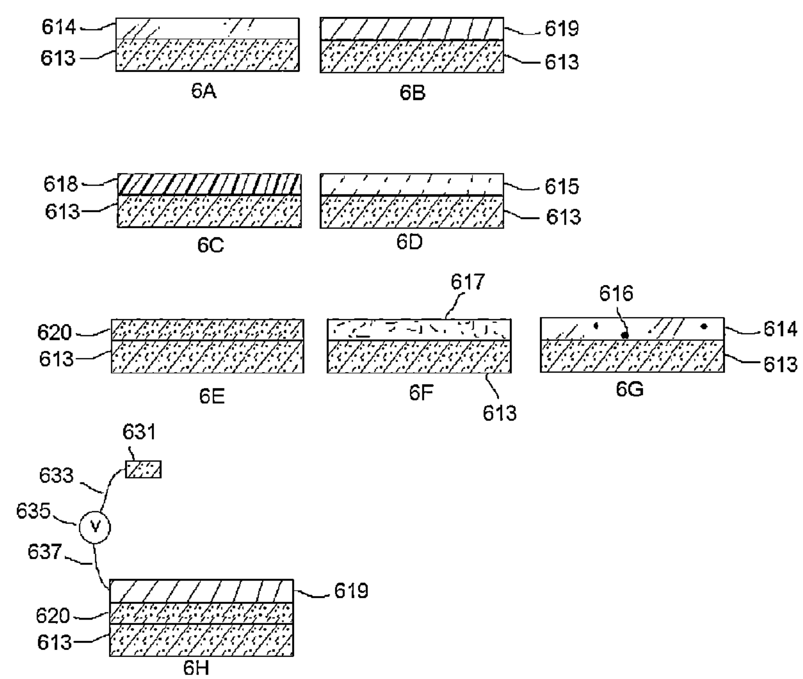

FIGS. 6A through 6G show section views of an imaging integrated circuit with coatings: transparent, wavelength-filtering or polarizing (FIG. 6A), metallic (FIG. 6B), plastic (FIG. 6C), transparent chemically resistant (FIG. 6D), non-conductor (FIG. 6E), adhesive (FIG. 6F), and transparent having fluorophores, scintillants or phosphors (FIG. 6G). FIG. 6H shows a section view of an assembly suitable for measurement or application of electric potentials.

Figure 7:
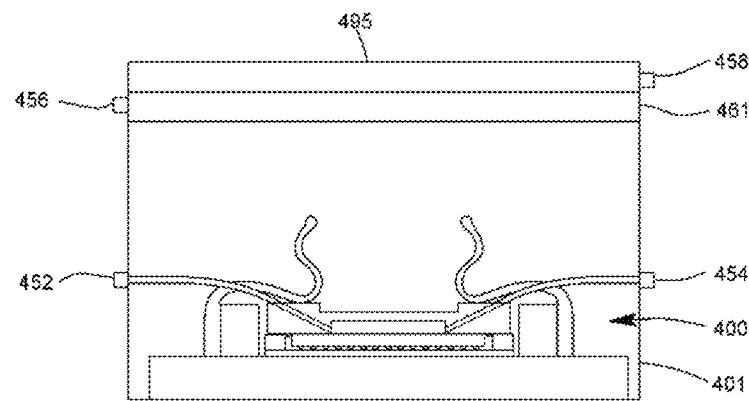

FIG. 7 shows a section view of an imaging device equipped with a portable multi-color light source and a housing with power, I/O, and fluid connectors.

Figure 8:
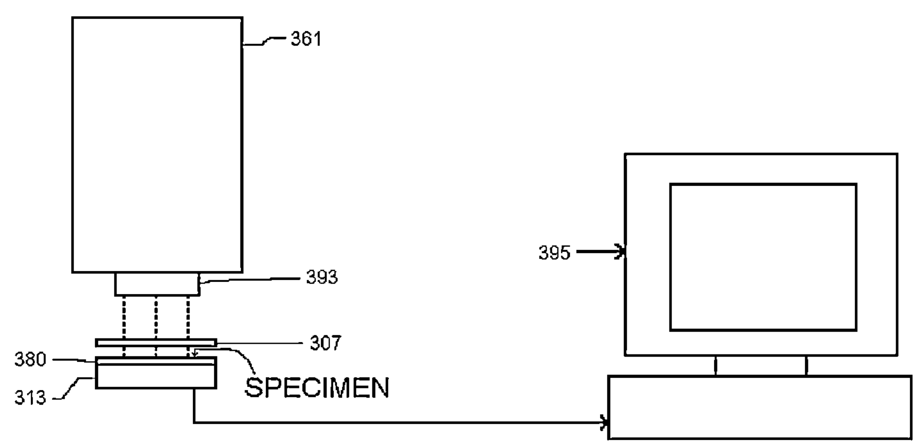

FIG. 8 shows a schematic of an imaging device and a computer-based system, with dashed lines indicating light along the optical path.

Figure 9:
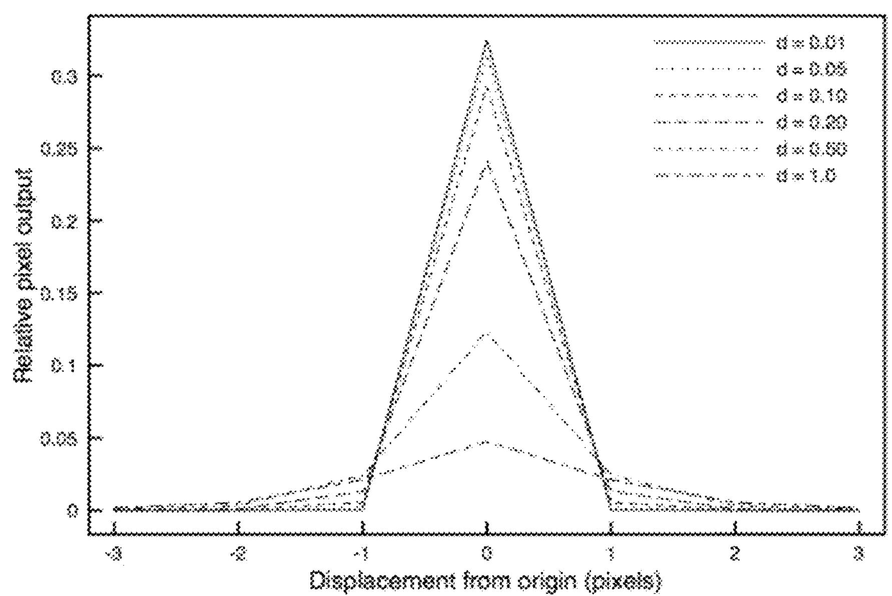

FIG. 9 shows a computed plot of a pixel response due to light from a point source passing into an imaging integrated circuit constructed in silicon at various distances from a center of a middle pixel (origin) as the distance (elevation) of the source above that center is increased. Distance, both laterally and above the surface, is measured in units of the width of a pixel. Each curve represents a relation for a specified vertical distance of the source above the photosensitive surface of the imaging integrated circuit, as indicated in the inset key.

Figure 10A:
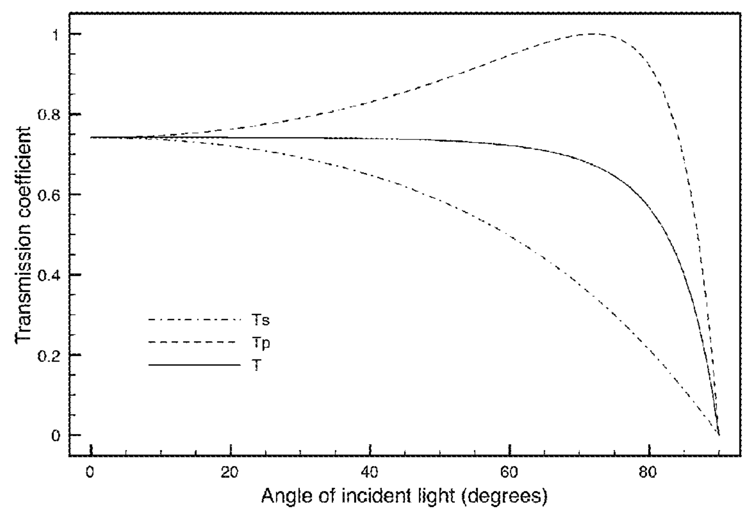
Figure 10B:
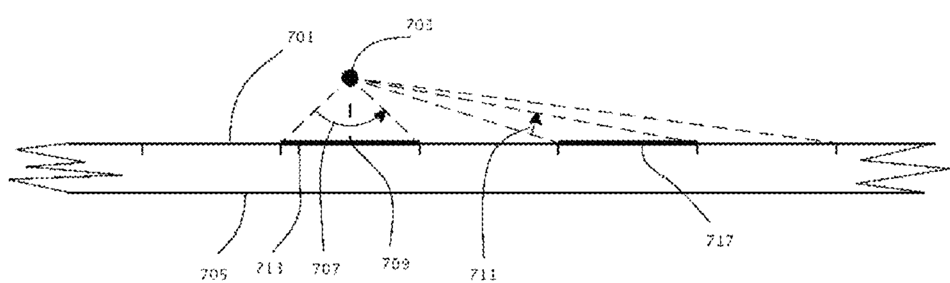

FIGS. 10A and 10B show (10A) transmission coefficients of the Fresnel formulas for angles between zero and ninety degrees; (10B) an illustration of decreasing pixel profile with respect to a light source as angle of light with respect to the surface normal increases.

Figure 11:
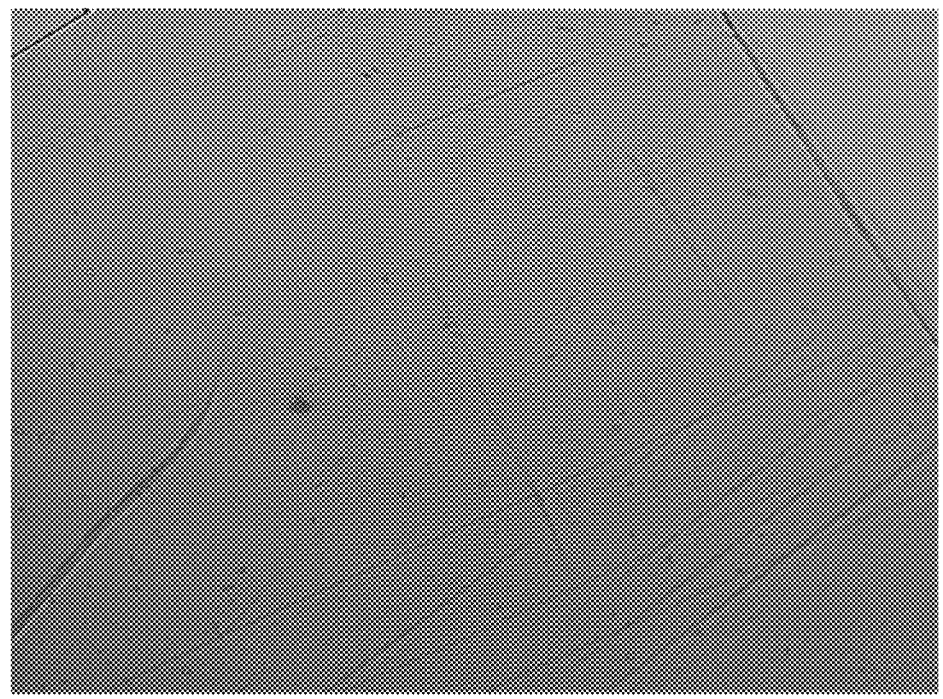

FIG. 11 is an image of a 30 μm-thick Mylar sheet, imaged using an apparatus referred to in the Examples, having 5.2 μm×5.2 μm pixels.

Figure 12:
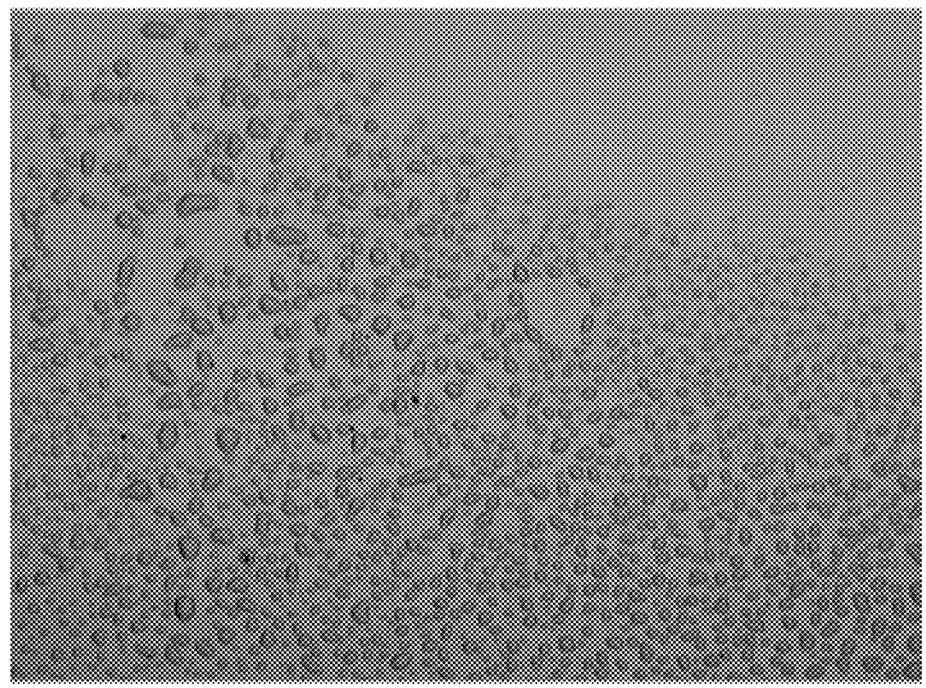

FIG. 12 is an image of micro-droplets in an aerosol of organic solvent, imaged using an apparatus referred to in the Examples, having 5.2 μm×5.2 μm pixels.

Figure 13:
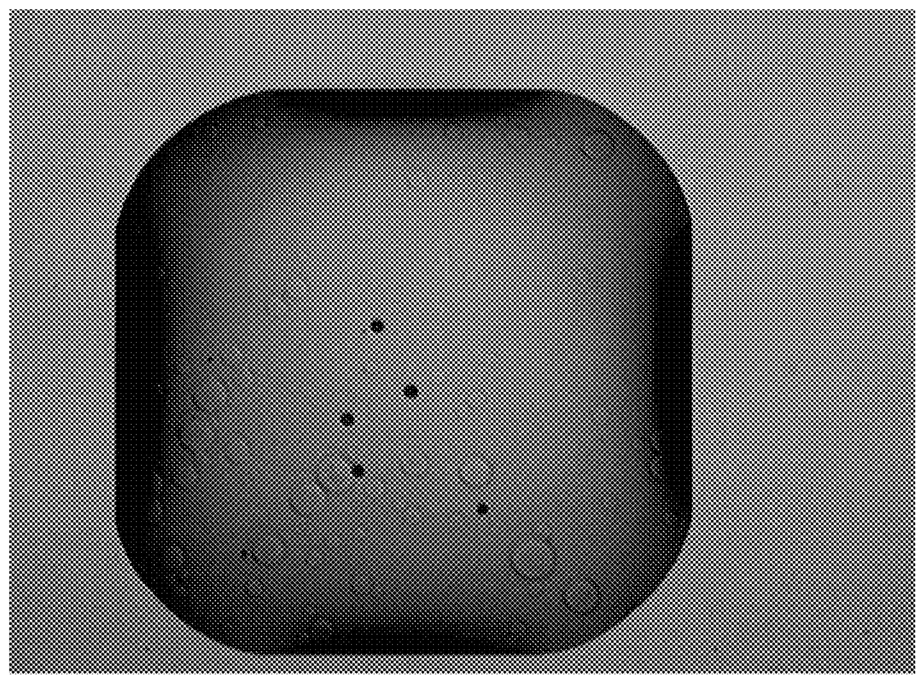

FIG. 13 is an image of a 1 μl droplet of water with suspended Sephadex beads of sizes ranging from <20 μm to >100 μm, imaged using an apparatus referred to in the Examples, having 5.2 μm×5.2 μm pixels.

Figure 14:
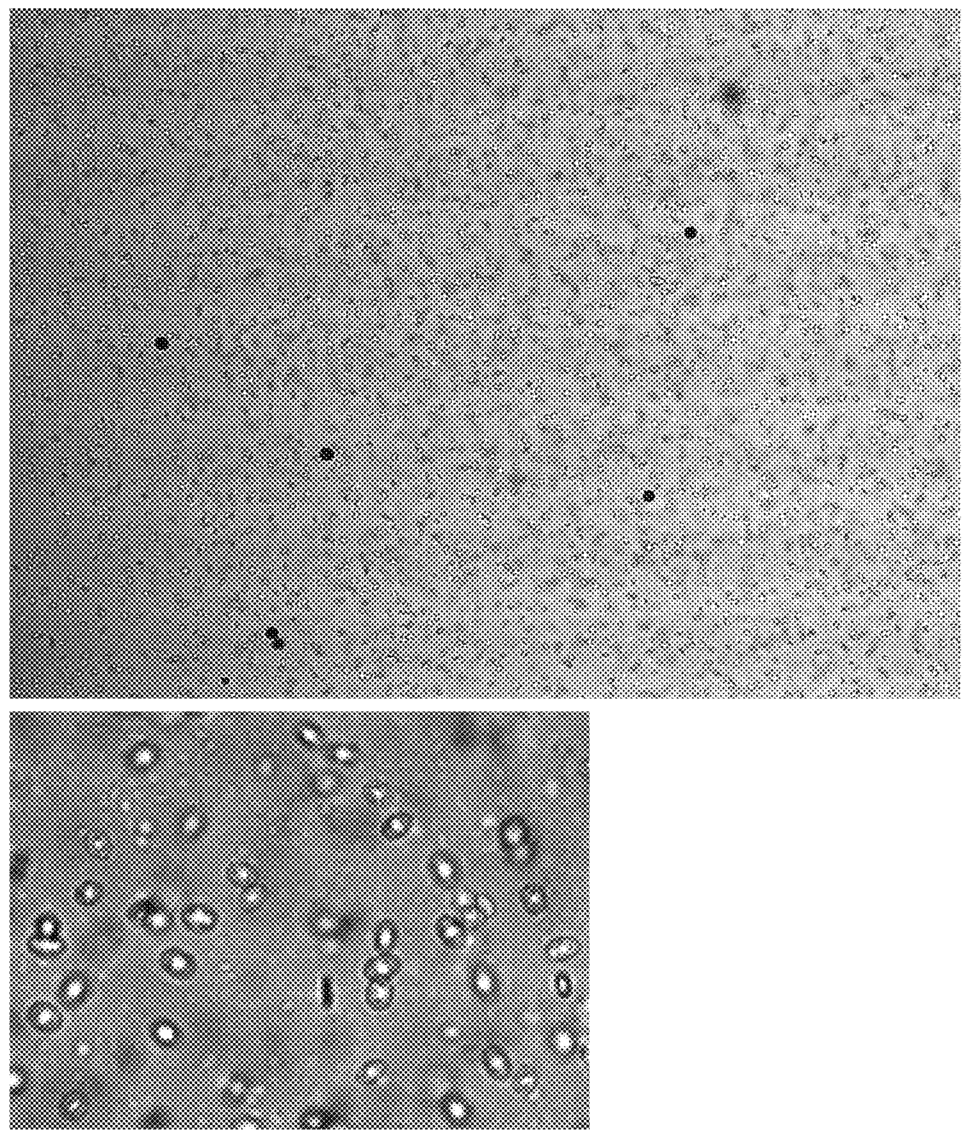

FIG. 14 is an image of a sample of fresh, living, unstained blood from an African clawed frog (*Xenopus laevis*), diluted in calcium-free Ringer's solution, imaged using an apparatus referred to in the Examples, with pixels 2.2 μm×2.2 μm. A full field of view (3.2×2.4 mm) is shown, along with a "zoomed in" view of part of the field of view, in which the elliptical shape and nucleated structure of the erythrocytes (long axis ~24 μm, short axis ~16 μm) is evident. The zoomed image has been enhanced by 2×2 pixel augmentation with bicubic interpolation.

Figure 15:
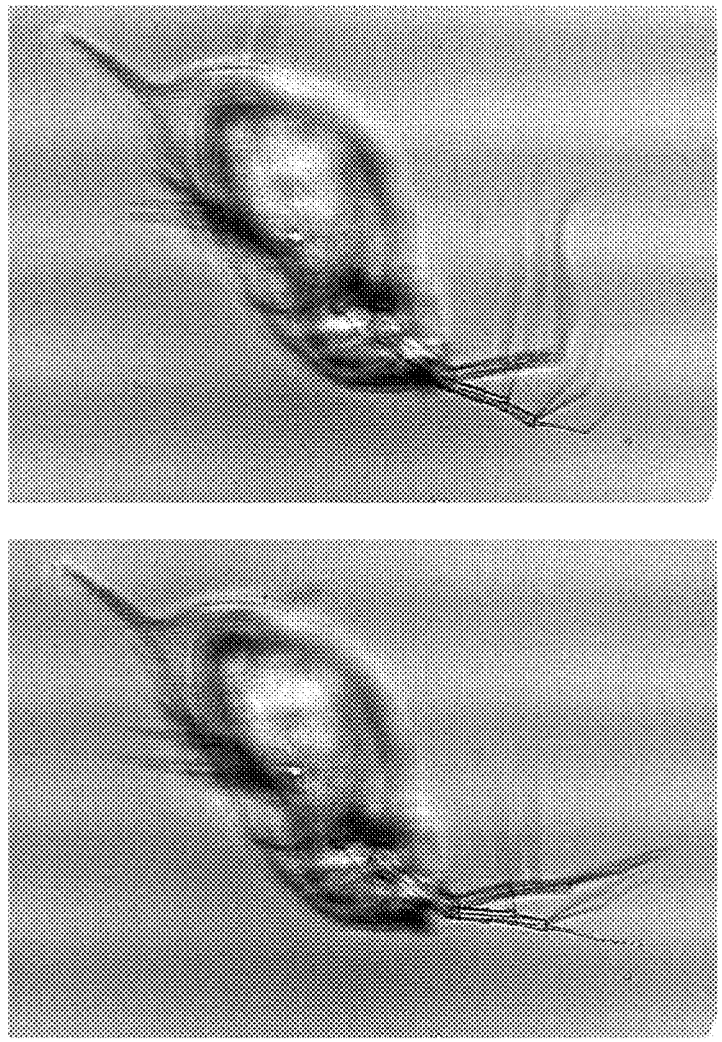

FIG. 15 is a portion of the field of view of two frames of a video sequence of a living water flea (*Daphnia* sp.), imaged using an apparatus referred to in the Examples, with pixels 2.2 μm×2.2 μm.

Figure 16:
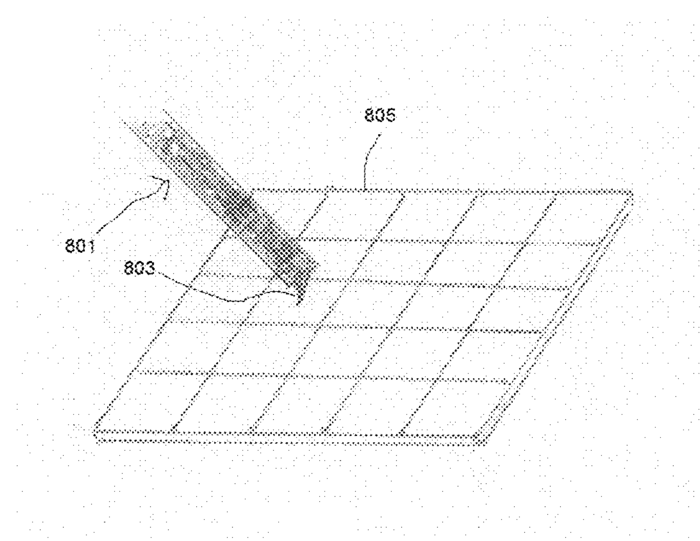

FIG. 16 shows a perspective view of an imaging device with an atomic force microscope.

FIGURE LEGEND

101 Specimen chamber
103 Chamber lid
105 Walls of chamber lid
107 Top of chamber lid
109 Rubberized gasket
110 Recess
111 Photosensitive surface
113 Imaging integrated circuit
115 Space
117 Locating block
119 Side of locating block
121 Opposite side of locating block
123 Spring clips
124 Base of spring clips
125 Mounting block
127 Printed circuit headboard
129 Shim
131 Solder pads
149 Waste chamber
151 Fluid flow system
152 Tubing
153 First fluid channel
154 First connector
155 Second fluid channel
156 Second connector
157 Pump
159 Reservoir
161 Light source
163 LEDs
165 Ambient light source
167 Portable multi-color light source
169 Display for portable multi-color light source
203 High-resolution photosensitive pixel array
205 Supporting circuitry
207 Pixel(s)
307 Cover
313 Imaging integrated circuit
361 Light source
380 Coating
393 Collimator
395 Computer-based system
400 Imaging device
401 Housing
452 Input connector for fluid flow system
454 Output connector for fluid flow system
456 Input/output connector
458 Power connector
461 OLED light source
495 Circuitry for input/output and illumination control
501 Temperature probe
503 pH probe
505 Heating element
507 Electrode
509 Second electrode
613 Imaging integrated circuit
614 Transparent coating, wavelength-filtering or polarizing material
615 Transparent chemically resistant material (diamond, $Al_2O_3$, $Si_3N_4$), transparent mechanically resistant material
616 Fluorophore, phosphor or scintillant
617 Adhesive coating
618 Plastic coating
619 Metallic coating, surface plasmon generating material, transparent surface electrode
620 Passivation layer
631 Transparent electrode
633 Wire
635 Voltmeter, input-switchable potential measuring/applying device
637 Wire
701 Photosensitive array having pixels
703 Point source of light
705 VLSI circuit
707 Angle
709 Origin
711 Second angle
713 Pixel immediately under light source
717 Pixel not immediately under light source
801 Atomic force microscope cantilever arm
803 Atomic force microscope tip
805 Imaging integrated circuit pixel(s)

Among other things, we describe an imaging apparatus that achieves resolution beyond the classical diffraction limits of conventional microscopy by utilizing an imaging integrated circuit having a high-resolution photosensitive array and supporting circuitry for readout. Spatial resolution is not limited by the diffraction limit as is inherent in most optical systems. No lenses or computational correction algorithms are required to produce high-resolution images.

The devices and methods described here can yield high-resolution images of a specimen without the need for lenses or computational image correction. Images are captured using an imaging integrated circuit having a high-resolution photosensitive array of pixels presenting a photosensitive surface, with supporting circuitry for readout, and associated computing equipment for data processing and user interaction. Light sources may be ambient or provided in an apparatus as appropriate. For parts of the specimen within half a pixel width of the photosensitive surface, the resolution of the image is limited by the size of the pixels making up the photosensitive surface. If the average width of these pixels is less than about half the wavelength of the light being used and the specimen is within half a pixel width of the photosensitive surface, then the near-field criterion may be satisfied and images can be obtained that equal or exceed the resolution of standard lens-based optical microscopes. The near-field criterion may be considered to be reached, for example, when the distance between the photosensitive surface and the specimen is less than the wavelength of interest.

Embodiments of imaging devices are illustrated by the examples shown in FIGS. 1, 2, 3, 4, 5, 6, 7 and 8. In some implementations, the imaging device may be oriented such that specimens are brought closer to the photosensitive surface by the force of gravity. In some embodiments, the imaging device is inverted or mounted on its side vertically, incorporating when necessary a restraint (not shown) for specimens in the specimen chamber. A cavity denoted specimen chamber 101 is formed by a chamber lid 103 having walls 105 and top 107, and by a photosensitive surface 111 presented by an imaging integrated circuit 113.

In some examples, the chamber lid may be made of any material that is rigid enough to resist warping or cracking under pressure. In some embodiments, the chamber lid 103 is at least partially transmissive of light. In some embodiments, the walls 105 are made of opaque material (examples include metal and ceramic) and the top 107 is either absent or made of transparent material. In some embodiments, the chamber lid 103 is made of glass or polystyrene and the top is between about 0.5 mm and about 1 mm in thickness. The walls of the chamber lid are of such dimensions and thickness as to approximately enclose the photosensitive surface in their inside dimensions and to approximately enclose the imaging integrated circuit in their outside dimensions. In some embodiments, the walls of the chamber lid are rectangular and each wall of the chamber lid has an inside length less than about 10 mm. The distance between the top 107 of the chamber lid 103 and the surface 111 is preferably between about 50 μm and about 1 mm, more preferably between about 75 μm and about 250 μm. In some embodiments, the top 107 achieves the desired specimen chamber height in the region of a recess 110 with respect to the height of the walls 105; in some embodiments, the recess is either absent, or no larger than necessary to receive a light source 161. A surface of the bottom 109 of the chamber lid 103 may be rubberized with a gasket or treated with a water-resistant microlayer, to assure a fluid-tight pressure-resistant seal when pressed down upon the non-photosensitive ceramic or plastic package of the imaging integrated circuit 113 by spring clips 123. The specimen chamber holds the specimen and medium in which the specimen is carried. For dry specimens, the medium may be air or some other gas or gas mixture appropriate to the stability or properties of the specimen. For liquid specimens or specimens suspended or dissolved in liquid, the medium is an appropriate liquid; the chamber need not be voided of gas in order to obtain images of such specimens.

In some embodiments, the chamber lid 103 incorporates one or more electrodes 631, positioned to contact the top of the sample chamber 101, electrically connected to a voltmeter or input-switchable potential-measuring or -applying device 635 by associated wires 637 (see FIG. 6B). Such electrodes may be fabricated as a thin layer of indium tin oxide or other substantially transparent conductive material. In some embodiments, the electrodes are fabricated, or contain, titanium nitride; methods for production of transparent and conductive thin films of titanium nitride are described in, e.g., Masato Kiuchi and Akiyoshi Chayahara (1994) "Titanium nitride for transparent conductors" Appl. Phys. Lett. 64: 1048-1049; incorporated here by reference. In some embodiments, the electrodes also are fabricated with, or contain, platinum black. In some embodiments a single electrode 631 covers substantially all of the chamber 101. In some embodiments, there are multiple electrodes 631 and wires 637 arranged in a matrix for efficient coverage of substantially all of the chamber 101. In some embodiments, the input-switchable potential-measuring or -applying device 635 allows for addressable measurement and/or application of potential across any or all of the electrodes 631. In some embodiments, the device 635 is a MED64 system and the matrix of electrodes 631 is a "MED probe" or similar multi-electrode array adapted for installation in the chamber lid 103. MED64 systems, MED probes, and the electrodes incorporated in them are available from by Alpha Med Scientific, Osaka, Japan (http://www.med64.com). The technical and manufacturing specifications and Web sites describing these products are incorporated by reference here.

In some embodiments, a matrix of electrodes 631 is arranged in an 8×8 grid, in which each electrode has about a 50×50 micron area positioned in a 150, 300, or 450 micron spacing configuration. In some embodiments, the wires 637 attached to their respective electrodes 631 are themselves substantially transparent conductive layers, separated by insulating material and embedded in a transparent substrate to allow for independent electrical conduction to each electrode and to a ribbon cable connecting the wires 637 to the device 635. In some embodiments, the matrix of electrodes 631 is a multi-electrode array produced by Multi Channel Systems, Reutlingen, Germany.

The imaging integrated circuit 113, a very-large-scale integrated (VLSI) circuit, has a high-resolution photosensitive array 203 including a two-dimensional array of pixels presented at its surface 111, surrounded by non-photosensitive supporting circuitry 205 for readout. The imaging integrated circuit 113 (including packaging) is electrically and mechanically attached to the headboard 127, which is a printed circuit board whose components connect to circuitry on the mounting block 125. The imaging integrated circuit 113 makes electronic and mechanical connection to the headboard 127 by means of a multiplicity of solder pads 131. Integrated circuit packaging for such purposes includes but is not limited to ball grid arrays, quad flat packs, and leadless chip carriers. The array 203 is made of materials used in very-large-scale or larger integrated circuits; in some embodiments, the array is substantially germanium, gallium nitride, or gallium arsenide. In some embodiments, the array is substantially silicon. In some embodiments, the high-resolution photosensitive array comprises a charge-coupled device (CCD); in other embodiments, the high-resolution photosensitive array is fabricated in CMOS. As an illustrative example, the OmniVision OV5642 imaging integrated circuit has area dimensions approximately 6.96 mm×6.71 mm, surrounding a photosensitive array approximately 3.67 mm×2.73 mm in area. This array is near centered, having a center with respect to the IC center (0,0) at about (220, 445) μm.

The chamber lid 103 is positioned in place within a space 115 defined by a rectangular locating block 117. Both the locating block 117 and the imaging integrated circuit 113 on its headboard 127 are situated atop the mounting block 125. The mounting block 125 is large enough in area to accommodate the dimensions of the locating block plus the spring clips 123. The locating block 117 is bonded to the mounting block 125 by means of solder, adhesive, or screws. In some embodiments, the locating block is made of a rigid, opaque material (examples of which include plastic, metal, or fiberglass) of about 1-2 mm thickness, with length dimensions of at most about 0.5 mm larger than those of the chamber lid walls. Two or more adjacent spring clips 11 are bonded to mounting block 125 at their bases 124, and they overlay locating block 117 and at least part of the walls 105 of the chamber lid 103, holding the lid in place inside the space 115. There are two spring clips 123 on each of two opposite sides 119, 121 of the locating block. The spring clips on each side are oriented in parallel and are of such shape as to facilitate insertion and removal of specimens and the chamber lid 103 when not in operation, but to maintain the lid in place during operation. In some embodiments, the spring clips are metal. In some embodiments, the spring clips are plastic. In some embodiments, the chamber lid is held in the space by means of other fasteners such as, for example, screws or slides adapted to the inside of the locating block. The outside edge of the imaging integrated circuit 113 is surrounded by a rectangular shim 129 of height approximately equal to the circuit's height and thickness equal to the remainder of the space 115 not occupied by the imaging integrated circuit. The shim 129 is made of suitable shimming material; as examples, the shim can be made of plastic, phenolic, fiberglass, or metal. The shim 129 is bonded to the mounting block 125 by means of solder, adhesive, or screws; it is also bonded to the outside edge of the imaging integrated circuit 113 by means of injected latex, silicone, plastic (preferably polystyrene), or adhesive so as to maintain a fluid-tight seal with the imaging integrated circuit.

One or more angled fluid channels are situated each having one lower end opening into the specimen chamber and the other, upper end positioned so as to allow flow of liquid specimen into or out of the specimen chamber, as appropriate. In some embodiments, there is a first fluid channel 153 and a second fluid channel 155 situated opposite each other within the walls 105 of the specimen chamber 103. These fluid channels have diameter slightly less than the height of the specimen chamber. They are, for example, cylindrical and oriented at an angle, for example, about 45 degrees with respect to the surface 111, permitting passage of fluid from the outside of the device into the specimen chamber. In some embodiments, a fluid flow system 151 is connected to fluid channels 153, 155 by tubing 152 and respective connectors 154,156, e.g. micro-Luer-Lok hubs. The fluid flow system 151 includes the tubing 152, a pump 157 that is preferably reversible and capable of variable flow rate, a reservoir 159, and a waste chamber 149. The tubing is preferably fused silica or plastic. In some embodiments, there are several pairs of fluid channels and associated fluid flow systems for flow cytometry and sorting applications.

A specimen may be placed into the specimen chamber 101, either by temporarily removing the chamber lid 103 to give access to the specimen chamber, or, particularly in the case of liquid specimen, by inserting the liquid specimen through one of the fluid channels 153, 155. Liquid specimens could be blood or other cells or microorganisms, seeds, pollen, spores, particles, droplets, crystals, sediments or other materials, suspended in water, saline or other aqueous solutions, or any other sufficiently fluid and non-viscous inorganic or organic fluid. Such liquid specimens may be static, or can flow through the chamber during imaging, driven either by negative or positive pressure provided by a micro-pump, syringe, gravity, surface tension, rotating discs or any other suitable motive source. Such liquid specimens could be input using a micropipette, a syringe or another such loading device, by deposition of a droplet onto the inlet, or by connection of a fluid reservoir.

Specimens may be, among other things, organic or inorganic, living or dead, dry or in liquid, and also combinations of those. Specimens, which depend on the resolution of the particular embodiment, can include but are not limited to proteins, DNA, RNA, nanomaterials, nanoscale structures, thin sections prepared by microtome or ultramicrotome, polymers, saccharides, lipid vesicles, biological cells, tissue samples, histological sections, micro-organisms, viruses, and combinations of those specimens. In some embodiments, seeding of a living specimen such as a cell onto the photosensitive surface or associated substrate or coating will allow for real-time or time-lapsed imaging of cell growth, movement, or other dynamic behavior. In some embodiments, specimens are stationary. In some embodiments the specimens may be caused to flow across the photosensitive surface by use of fluid channels attached to pumps and reservoirs. In some embodiments, there is at least a pair of fluid channels. In some embodiments, there are three or more fluid channels, the number being governed by the flow characteristics that are suitable for the application. In some embodiments, fluid flow is actuated by positive pressure; in some embodiments, fluid flow is actuated by negative pressure. Such an arrangement may be useful in the evaluation of disease states as imaged from cell suspensions or bodily fluids, including but not limited to blood, lymph, semen, bile, and urine. In some embodiments, the imaging integrated circuit outputs images to a computer comprising appropriate software for flow cytometry.

In some embodiments, placement of the specimen is manual; in the absence of a chamber lid, placing a specimen directly on the photosensitive surface will automatically satisfy or approximately satisfy the conditions for pixel-limited resolution for at least some part of the specimen; if the distance between at least part of the specimen and the photosensitive surface is less than the wavelength of light, the near-field criterion is also satisfied. In some embodiments, of interest for specimens in liquid, the specimen is placed on the imaging integrated circuit or substrate using a fluid flow system for movement and flow-through imaging of the specimen as it passes the imaging integrated circuit. Such a fluid flow system can comprise a simple system for liquid specimen placement and removal, such as a droplet of a specimen manually applied to the imaging integrated circuit, and a blotting paper oblique to the imaging integrated circuit and in contact with the specimen so as to soak up the liquid over time. In other embodiments, such a fluid flow system comprises a pump or other appropriate means for pulling/pushing the specimen; and a specimen-containing conduit, at least a segment of which (namely, the segment in the optical path) is substantially transmissive to a predetermined wavelength.

Images of the specimen can be obtained in the presence of the light source 161. The light source 161 produces at least one wavelength for which the imaging integrated circuit 113 is responsive. In some embodiments, the light source includes a laser and the predetermined wavelength is the substantially monochromatic wavelength of the laser. In some embodiments, the light source includes a blackbody and the predetermined wavelength band is a segment of the electromagnetic spectrum which the blackbody is suitably efficient at producing, with or without use of a bandpass spectral filter interposed between the light source and the specimen. In some embodiments, the light source comprises one or more light-emitting diodes 163, for example, an organic light-emitting diode array, oriented so as to produce light in the predetermined wavelength band or bands. In some embodiments, the light source is continuous. In some embodiments, the light source is pulsed. In some embodiments, the light source is polarized. In some embodiments, the light source may be placed on the tip of a nanoscale probe. In some embodiments, the light source includes any ambient, incandescent, or fluorescent light source, including light produced by the sun 165. In some embodiments, the light source is structured, such as a periodic grating of bright bars. In some embodiments, there may be additional light sources. In conjunction with appropriate oblique, pulsed, polarized, structured, or other forms of illumination, some embodiments can generate additional useful information corresponding to methods known in the art of microscopy, including but by no means limited to dark field, fluorescence, fluorescence lifetime, optical tomography, and polarization microscopy. In some embodiments, the specimen is itself the light source 161; for example through chemiluminescence, or because the photosensitive array is treated to render it sensitive to radiation emitted by a radioactive specimen. In some embodiments, the light source is part of a portable electronic device capable of multi-color light emission 167, such as a smartphone. In some embodiments, the smartphone has a high-intensity organic light-emitting diode display 169 that allows for illumination at different wavelengths and positions relative to the photosensitive surface, with independently controlled onset and duration and capable of simultaneous light source control so as to approximate a uniformly diffuse source.

The spectra of the light source(s) may lie in any predetermined region of the electromagnetic spectrum detectable using photosensitive arrays, with or without specialized treatments to extend the effective ranges of wavelengths detectable by such arrays. In some embodiments, the predetermined wavelength or wavelength band is in the infrared spectrum. In some embodiments, the predetermined wavelength or wavelength band is in the ultraviolet spectrum. In some embodiments, the predetermined wavelength or wavelength band is in the visible spectrum. In some embodiments, the predetermined wavelength or wavelength band is in the X-ray spectrum. In some embodiments, the predetermined wavelength or wavelength band is in the microwave spectrum. In some embodiments, the predetermined wavelength or wavelength band is approximately that which has a frequency between about 1 Terahertz and about 1,000 Terahertz. Combinations of light in two or more bands may be used in some examples.

In some embodiments that are pertinent, for example, to fluorescence microscopy, the light source produces light substantially in the far ultraviolet spectrum, for example below 300 nm, and the photosensitive surface is inherently, or by application of appropriate coatings, insensitive with respect to the far ultraviolet, such that excitation of a specimen does not produce a signal, but the longer-wavelength fluorescence or phosphorescence of the specimen does produce a signal.

In some embodiments, the light source is a rapidly modulated source such as an LED that produces light within the excitation band of the specimen and substantially within the absorption band of the photosensitive surface. The imaging integrated circuit is switched off during excitation to avoid recording a signal during excitation, and is rapidly turned on again in time to record fluorescence (for example, decaying over nanoseconds or tens of nanoseconds) or phosphorescence (for example, decaying over milliseconds or longer) signals. This modality may be of use in, for example, fluorescence lifetime imaging (FLIM).

In some embodiments, the light source includes individually controlled light-emitting diodes (LEDs) selected for their spectral emission characteristics and their uniformity of emitted light, and positioned so as to facilitate the analyses contemplated. In some embodiments, the light sources are positioned so as to uniformly illuminate the specimen chamber. The LEDs are controlled, for example, by either an embedded controller incorporated within the instrument or by a microprocessor contained in smartphones or other commercially-available, "off-the-shelf" computing devices. The LEDs will be controlled, for example, either singly or in groups so as to facilitate the analyses to be contemplated, including but not limited to conventional microscopy wherein the illuminator, the specimen and the imaging system are substantially aligned, and dark-field microscopy wherein the specimen is illuminated from an angle outside the acceptance angle of the pixel. In addition, through appropriate selection of the LEDs in the illuminator, the contemplated contact microscope can be used for, but not be limited to, e.g., color imaging, fluorescence microscopy, polarization microscopy, infra-red and ultra-violet microscopy. Some embodiments will incorporate multiple illuminators, each of which may have different characteristics so as to facilitate the conduct of a wider range of analyses. In some embodiments the illuminators will be easily interchangeable. In some embodiments the illuminators may include organic LED (OLED), passive matrix organic LED (PMOLED) or active matrix organic LED (AMOLED) panel with selective addressing. Some embodiments facilitate both uniform specimen illumination and rapid illumination variation so as to facilitate analyses yet to be contemplated with both stationary and moving specimens. In some embodiments, an AMOLED panel may be used to illuminate the specimen through appropriate control of the panel photoemitters. In some examples, the illuminator can include LEDs, organic LED panels, fluorescent panels, x-ray sources, ultraviolet sources, ambient illumination such as sunlight or room light, incandescent sources, or any other light source, including none, e.g., for chemiluminescent specimens, and combinations of these examples. Configurations of the sources include, but are not limited to, flat panels, rectangular or other grid layouts of sources, movable sources, multi-color sources, and sources affixed to the inside or a hemispherical shell mounted over the specimen chamber with the centre of the chamber as the center of the shell, or combinations of them. Control of the illumination sources may include, but not be limited to, steady illumination, selectively exciting one or a plurality of illumination sources simultaneously or in sequence, controlling the intensity of any one or a plurality of sources, controlling each or a plurality of sources so as to have a specific temporal illumination pattern, or using any one or any combination of them and others (including future technologies). The controller for the illumination may include, but not be limited to, a manual controller such as a switch or knob, an automated embedded computing system, an external computing system such as a smartphone, an external computing system such as a desktop or laptop computer, or a combination of the foregoing.

FIG. 7 illustrates features of some embodiments. In some examples, the imaging device 400 is placed in a housing 401 with a hinged lid, by which hinge dry specimens may be inserted and removed. On the underside of the lid, an organic LED light source 461 illuminates the specimen. Integral to the lid and bonded to the light source 461 is the circuitry 495 for input/output and illumination control. Power connector 458 is attached to the circuitry 495. Input/output connector 456, preferably a USB interface, is attached to the circuitry 495 adjacent to the light source 461. Paired fluid flow connectors 452, 454 attach to a fluid flow system akin to that in FIG. 4. The form factor of the entire embodiment of FIG. 7 can be about that of a smartphone, for example.

FIG. 8 illustrates the flow of light and output data when an embodiment of an imaging system is in operation. A light source 361 produces light in, for example, a predetermined wavelength or wavelength band. In some embodiments, a collimator 393 having a lens, filter, or combination thereof ensures that the light is collimated along an optical path and is composed of substantially only wavelengths of the predetermined wavelength or wavelength band. Light travels along the optical path toward the imaging integrated circuit 313. In some embodiments, the angle of incidence of the light onto the imaging integrated circuit will be oblique, rather than normal. In some embodiments, an optional cover 307 substantially transmissive to the predetermined wavelength or wavelength band restricts the specimen volume or protects the specimen from unintended movement or exposure. The specimen is illuminated, and the resultant light produces an image in the optical path beyond it. In some embodiments, an optional coating 380 lies between the specimen and the imaging integrated circuit 313. The resultant image as captured by the imaging integrated circuit 313 is outputted to a computer-based system 395 for storage, readout, or analysis.

In our discussion we use the term “high-resolution” to refer, for example, to a resolution that equals or exceeds the resolution of standard lens-based optical microscopes. For example, depending on the context of the application, high-resolution can mean less than 5 μm, less than 2 μm, less than 1 μm, less than about 0.5 μm, or even less. Resolution is primarily determined by the pixel size of the photosensitive array. Some photosensitive arrays have many million square pixels each slightly more than 1 μm on a side, resulting in a resolution of about 1 μm; the resolution achievable will improve with decreasing pixel sizes, theoretically exceeding, for example, 1 billion pixels, each as small as 200 nm or less on a side, as the design and fabrication techniques of integrated circuits or other devices improve. The number, shape, and arrangement of pixels in the array is arbitrary, with no intrinsic limit, and can be predetermined for manufacture based on the corresponding application of interest. In some embodiments, the longest pixel dimension is 10 μm or smaller. In some embodiments, the longest pixel dimension is 5 μm or smaller. In some embodiments, the longest pixel dimension is 1 micron or smaller. In some embodiments, the longest pixel dimension is 500 nm or smaller. In some embodiments, the longest pixel dimension is 250 nm or smaller.

Imaging integrated circuits can be constructed that have pixel sizes smaller than the wavelength of visible light, as shown, for example, in U.S. Pat. No. 7,153,720, incorporated here by reference. In some embodiments, the imaging integrated circuit includes a charge-coupled device (CCD). In other embodiments, the imaging integrated circuit is fabricated using complementary metal-oxide semiconductor (CMOS) technology. CCDs have advantages for contact optical microscopy applications, including the ability to detect light over the full exposed surface of the chip (100% fill factor), though they have slower readout speeds relative to CMOS due to requirement for sequential transfer of charge from light-sensing (parallel register) to readout (serial register) elements. Various configurations of CCD can be used: full-frame architecture is desirable to maximize the proportion of the chip available for imaging, but requires an external shutter to prevent image smearing during readout; whereas frame-transfer architecture avoids image smearing, but in the process requires a masked, non-photosensitive area of the parallel register of about the same size as the photosensitive area of the parallel register, with the result that the imaging integrated circuit has about half the photosensitive area of a full-frame architecture. Because of the small area of the individual pixels in the arrays used in this invention, the charge collected in each pixel will be small under many imaging conditions; however, as the specimen is in contact, or nearly in contact, with the pixel, the pixel’s effective acceptance angle for photons emanating from the specimen is larger than that achieved by lenses in conventional microscopy. In some CCD embodiments, to increase the sensitivity further, CCDs of any architecture may additionally employ electron multiplying gain, in which high clock voltages applied to an extended region of the serial register(s) amplify the charge of each pixel as it is shifted to the output node(s).

CMOS devices have alternative advantages for these applications, including less expensive fabrication, signal processing (including amplification) by electronic elements embedded in individual pixels, and the ability to read out independently-addressed pixel values individually without sequential transfer. In some CMOS embodiments, thinned back-side illuminated arrays are used; though previously requiring expensive and complex fabrication methods, these can now be fabricated cheaply using bonded wafer processes such as those that use silicon-on-insulator substrates with a buried oxide layer as an etch-stop to yield a uniformly optimally thinned light-absorbing back layer (see as an example, U.S. Pat. No. 7,425,460, incorporated here by reference). Light entering ordinary (front-side illuminated) imaging integrated circuits typically passes through overlying layers that scatter light and whose metal circuit elements block the underlying photosensitive layer; in back-side illuminated imaging integrated circuits the photosensitive layer is close to the surface, above the metal circuit-bearing layers, typically resulting in less light blocking (larger “fill factors”) and consequently higher effective quantum efficiency.

In some embodiments, the imaging integrated circuit is windowless. Most commercially available imaging devices have a protective window over the CCD or CMOS, and typically this window must be absent in order for the specimen to come close enough to the photosensitive surface to achieve high resolution, as defined above, without computational image processing. When a point on the specimen is less than half a pixel width from the center of the closest pixel, nearly all the light emitted or scattered from that point toward the array will predominantly be incident on, and therefore excite, only the closest pixel; under these conditions, resolution is determined by the pixel size or, more precisely, by the size of a circle of equivalent area (i.e., ~450 nm resolution for a 400 nm×400 nm pixel), although resolution may be further enhanced by computation, specimen flow, or other means. No lenses or any other optical components are required to achieve these conditions, and thus to achieve such pixel-limited resolution.

Specimens or parts of specimens farther from the photosensitive surface are not imaged as sharply, due to the spread of light between the specimen and the photosensitive surface. As the distance between a point light source and the photosensitive surface of the array is increased, the image of the point at the photosensitive surface exhibits increasing blur, as light from the point impinges upon, and excites, additional pixels beyond the pixel directly below and nearest to the point. The extent of that spread to additional pixels is governed by two considerations that limit the angle of acceptance of light by the pixels (where angle of acceptance refers to the maximum deviation of a ray from the surface normal at which the ray can influence the pixel output).

Firstly, as the angle of incidence of light onto the photosensitive surface with respect to the surface normal is increased, an increasing portion of the light is reflected, until an angle is reached beyond which all the light is reflected. This relationship is defined by the Fresnel formulas as follows:

$$R_s = \left[\frac{n_1\cos\theta_i - n_2\sqrt{1-\left(\frac{n_1}{n_2}\sin\theta_i\right)^2}}{n_1\cos\theta_i + n_2\sqrt{1-\left(\frac{n_1}{n_2}\sin\theta_i\right)^2}}\right]^2$$

$$R_p = \left[\frac{n_1\sqrt{1-\left(\frac{n_1}{n_2}\sin\theta_i\right)^2} - n_2\cos\theta_i}{n_1\sqrt{1-\left(\frac{n_1}{n_2}\sin\theta_i\right)^2} + n_2\cos\theta_i}\right]^2$$

where $R_s$=reflection coefficient for s-polarized light $R_p$=reflection coefficient for p-polarized light $\theta_i$=angle of incident ray with respect, to surface normal $n_1$=index of refraction for region containing light source $n_2$=index of refraction for imaging array The transmission coefficients are:

$$T_s = 1 - R_s$$

$$T_p = 1 - R_p$$

$$T = \frac{T_s + T_p}{2}$$

where $T_s$ is the resultant transmission coefficient for s-polarized light, $T_p$ is the resultant transmission coefficient for p-polarized light, and T is the resultant transmission coefficient for unpolarized light. The transmission coefficients are plotted in FIG. 10(*a*) for angles between zero and ninety degrees. From the figure it is seen that about 75 percent of unpolarized light is transmitted up to angles of about 60 degrees, after which point transmission falls off sharply.

Secondly, as the angle of light incidence with respect to the surface normal increases, the pixel poses a decreasing profile with respect to the light source.

This situation is shown in FIG. 10(*b*). In the figure, a point source of light 703 is positioned above the center of a pixel 713 that is part of a photosensitive array having pixels 701 that constitutes the photosensitive part of an imaging VLSI circuit 705. The center of the pixel 713 under the point light source 703 is the point of the photosensitive pixel array 701 closest to the point light source 703 and is denoted the origin 709 of the coordinate system used in the analysis. The light emitted from said point source is emitted in all directions equally. The light that falls on the pixel 713 immediately under said point light source receives an amount of light that is proportional to an angle 707 subtended by the area of the pixel at the said point light source. Similarly, the light received by any other pixel in the array, e.g., pixel 717, is proportional to an angle 711 that it subtends at the said point light source. For each pixel, the angle subtended at the point light source is a function of the pixel area projected toward the point light source and the distance from the point light source to said pixel.

The projection of the pixel area in the direction of the source is:

$$A_p = mn\frac{d}{\sqrt{d^2 + r^2}}$$

where d is the distance of the point source above the photosensitive surface, m and n are the x and y dimensions of each pixel respectively, and r is the distance from the point along the photosensitive surface to the pixel of interest. This projected area subtends a solid angle at the source given by:

$$\omega = \frac{mnd}{(d^2 + r^2)^{3/2}}$$

and so the proportion of the light flux emitted by the source that falls on this projected area is:

$$I_i = \frac{I_s mnd}{4\pi(d^2 - r^2)^{3/2}}$$

where $I_s$ is the source light flux and $I_i$ is the incident intensity on the projected area of the pixel under consideration. The light that passes into the pixel is this light, further attenuated by the transmission coefficient due to the angle made by the light with the surface of the pixel. Thus, the light available for detection is:

$$I_p = T\frac{I_s mnd}{4\pi(d^2 + r^2)^{3/2}}$$

For example, consider a specimen in aqueous suspension overlaying the surface of a photosensitive array constructed in silicon. Using an index of refraction $n_1$ for water of 1.33 and for silicon $n_2$ of 4.08, which are approximately their respective indices at a wavelength of 550 nm, the computed spread of detected intensity of light emitted by a point source as a function of distance of the source from the silicon surface is shown in FIG. 9. Standard algorithms for image sharpening can utilize this data for improvement of image quality.

Tolerance for such blurring will depend upon the specific imaging application; in some cases, useful information can be obtained from specimen regions that do not satisfy the near-field criterion, such as specimens many micrometers or tens of micrometers from the photosensitive surface. In some embodiments, the distance between the specimen and the photosensitive surface is approximately equal to one of the following quantities: ten times the average wavelength produced by the light source, or less than five times the average wavelength, or preferably less than three times the average wavelength, or more preferably less than the predetermined wavelength, or still more preferably less than half the predetermined wavelength.

In some embodiments, some of the supporting circuitry for readout is contained within the imaging integrated circuit. In some embodiments, the supporting circuitry is coupled to additional supporting circuitry or microprocessors that control the functions of the integrated circuit, such as gain or data clock rate. In some embodiments, the imaging integrated circuit is commercial and off-the-shelf, having a high-resolution photosensitive array, supporting circuitry for readout, and an industry-standard interface for connection to a computer-based system for image data display, storage, and analysis, for example, the Aptina MT9E013, the OmniVision OV14825, and the OmniVision OV14810; the technical data for which are incorporated here by reference. As an illustrative example, the OmniVision OV5642 incorporates the full functionality of a single chip, 5 megapixel digital camera with 1.4 micron pixel widths, including output of images at 15 frames per second (fps) in RAW RGB mode and up to 60 fps in 1080i resolution. The OV5642 supplies images for readout via serial camera control bus (SCCB) and mobile industry processor (MIPI) interfaces using digital video parallel and MIPI serial ports. It also supports output in RGB565/855/444, CCIR656, YUV422/420, and YCbCr422 modes. The signal descriptions, pad numbers, and corresponding block and pad diagrams for OV5642 illustrate a preferred implementation for an imaging integrated circuit; these are hereby incorporated by reference to the OmniVision OV5642 datasheet and product specification version 2.03. Computer-based systems that are capable of connection to the supporting circuitry may be embedded or standalone, purpose-built or off-the-shelf, including, for example purpose-designed embedded computing systems, smartphones, portable computers, and netbooks.

In some embodiments, the computer-based system has firmware or software for image analysis, storage, illumination control, and display. Such firmware or software has previously been paired with optical microscopes and digital camera technology. In some embodiments, the computer-based system implements algorithms to enhance, detect, analyze, characterize, and measure images of cells and other specimens of interest and to display or transmit the result of these algorithms to a human operator and/or a second computer-based system, such as a smartphone or storage system including hospital record storage systems. In some embodiments, the computer-based system implements enhancement algorithms that can identify images of discrete specimens in smooth flow in a series of time-lapsed images.

In some embodiments, the imaging integrated circuit's supporting circuitry is coupled to additional circuitry on the mounting block. In some embodiments, the mounting block incorporates certain interfaces in hardware that are capable of supplying the RAW, RGB, and/or TWAIN standard. Examples of interfaces for optical microscope cameras that could be adapted include those included in the Jenoptik ProgRes Professional Color CCD Firewire Camera; the Luminera Infinity Color CCD or CMOS USB-2 Cameras; and the Motic Moticam Color CMOS USB-2 Camera; the technical data and owner's manuals for which are incorporated here by reference. In some embodiments, a computer-based system is coupled to the mounting block interfaces for imaging analysis, display, and storage. Examples of imaging analysis software that could be used include ProgRes CapturePro, Infinity Capture and Infinity Analyze, and Motic Images Plus; the technical data and owner's manuals for which are incorporated here by reference. In some embodiments, the image captured by the imaging integrated circuit is outputted to a storage medium. In some embodiments, the image captured by the imaging integrated circuit is outputted to a real-time display device. In some embodiments, only pixels of interest need be output from the imaging integrated circuit in order to maintain a desired high temporal resolution; CMOS-based imaging integrated circuits are well suited for this task but other architectures are possible. The raw data of pixel array intensities, or the post-acquisition images themselves, may be enhanced by various computational means including but not limited to deconvolution, pixel interpolation, spatial filtering, noise reduction, edge enhancement, and other methods. Moreover, in some embodiments, a suboptimal point-spread function (whereby light meant to be detected at a given pixel is also detected by an adjacent pixel) may be corrected computationally. In some embodiments of an imaging system, the imaging integrated circuit, associated electronics, and analysis device are integrated so as to be combined in a portable housing; the light source may be integrated, standalone, or supplied from ambient light, allowing for desktop-, laptop-, cellphone-, or smaller-sized microscopes as the desired application requires.

In some embodiments, there is a chamber lid that is substantially transmissive to at least one wavelength of light produced by a light source. The locating block is preferably a rectangle. The walls of the chamber lid may be square, rectangular, circular, elliptical, or some other shape appropriate to the specimen being imaged. In some embodiments, the top surface of the chamber lid is absent and a multi-colour light-emitting display surface forms the top of the specimen chamber. In some embodiments, the chamber lid and locator block are partially or substantially transparent or translucent. In other embodiments, the chamber lid and locator block are opaque; examples of applications for such a design include chemiluminescence imaging and autoradiography. In some embodiments, the specimen chamber lid is not present, as for microscopic imaging of the surface of large or thick specimens.

In some embodiments, the specimen chamber has a probe; examples of probes include temperature probe 501 and pH probe 503. In some embodiments, the specimen chamber has a pair or more of mounted electrodes 507, 509 along the perimeter of the chamber for applying transverse or longitudinal electric fields or for stimulation of specimens. Such an arrangement of electrodes may be used, as examples and in conjunction with appropriate fluid handling as described above, for electrophoresis, separation/sorting, determination of specimen surface charge, determination of zeta potential, cell stimulation, and specimen orientation. In some embodiments, the specimen chamber has a heating element 505. Such a heating element may be used, as examples, in the observation of time-dependent processes and in the incubation of live specimens for time-lapse imaging.

In some embodiments, the photosensitive surface has been treated with one or more thin layers. The layers may be considered thin when the aggregate thickness of such layers as applied to a photosensitive surface still allows for the near-field criterion to be satisfied or approximately satisfied. In some embodiments, the layers are thin enough for specimens to come within half a pixel width of the photosensitive surface. In some embodiments, the layers are thin enough in the direction of the optical path so that the total distance that the optical path takes through the layers is no more than about the wavelength of interest. In some embodiments, a thin layer of transparent chemically resistant material coats the photosensitive surface. Such a thin-film substrate may be any sufficiently transparent and insulating material, including but not limited to silicon oxide, titanium oxide, aluminum oxide, tantalum oxide, magnesium fluoride, lanthanum fluoride, aluminum fluoride, silicon nitride, and silicon oxynitride; and it may be deposited by a variety of means including but not limited to magnetron sputtering, chemical vapour deposition, thermal or vacuum arc plasma evaporation. In some embodiments, the substrate is a dielectric thin film acting as an interference filter, thereby restricting the spectral sensitivity of the underlying pixels as appropriate to a given application. In some embodiments, the substrate is used to effect certain forms of color imaging. In certain embodiments, the substrate is substantially transmissive to a portion of a predetermined wavelength band, such as a band-pass filter. In other embodiments such as for fluorescence or emission microscopy, the substrate 618 is substantially transmissive to an alternative predetermined wavelength band which corresponds to the wavelength band produced by fluorescence, emission, or in other ways, of the specimen. In some embodiments, the substrate includes a dielectric thin film acting as an anti-reflection coating. In some embodiments, there are multiple substrates situated in close contact to each other. In some embodiments, the photosensitive surface is silanized so as to decrease adhesion between the surface and the specimen. In some embodiments, the chemically resistant material 615 includes diamond, deposited in a suitably thin layer as, for example, by chemical vapor deposition. In some embodiments, the chemically resistant material includes $Al_2O_3$ or $Si_3N_4$, deposited in a suitably thin layer as, for example, by chemical vapour deposition. Such materials can impart more robust characteristics to the photosensitive surface, allowing for ease of cleaning as well as protection of the surface from abrasive specimens. In some embodiments, a passivation layer 620, typically of $Si_3N_4$, coats the imaging integrated circuit, resulting in reduced conductivity when used with metallic or other conductive samples such as salt solutions. Technology is available to deposit such filters as a thin film and in arbitrary pixel-by-pixel patterns. In some embodiments, the imaging integrated circuit incorporates a pixel-by-pixel array of microlenses as, for example, a light-collecting stage of sufficient thinness so as to allow the near-field criterion to be satisfied or approximately satisfied.

In some embodiments, a thin layer of polarizing material 614 coats the photosensitive surface. In some embodiments, a thin layer of absorptive material 614 coats the photosensitive surface. In some embodiments, a thin layer of interference material 614 coats the photosensitive surface. In some embodiments, a thin layer of surface plasmon generating material 619 coats the photosensitive surface.

In some embodiments, a passivation layer 620 coats the photosensitive surface and a thin layer of substantially transparent conductive material 619 coats the passivation layer. In some embodiments, the layer 619 may act as one or more surface electrode(s) in conjunction with one or more wires 637 electrically connecting the layer to a voltmeter or switchable potential-measuring device 635; in turn, one or more wires 633 electrically connects the device 635 to one or more respective transparent electrodes 631 mounted on the top of the chamber 101 to enable the measurement or application of an electric potential between any electrode 631 and the layer 619 (see FIG. 6H).

In some embodiments, the thin layer of conductive material 619 is indium tin oxide (ITO). Transparent electrically-conductive layers of ITO can be very thin, e.g., less than 350 nm, less than 100 nm, less than 50 nm, or less than 25 nm in thickness; and thus when, for example, deposited on the photosensitive surface may allow for the near-field criterion to be satisfied or approximately satisfied.

In some embodiments a single electrode 619 covers substantially all of the imaging integrated circuit 613. In some embodiments, there is a plurality of electrodes 619 and wires 637 arranged in a matrix for efficient coverage of substantially all of the imaging integrated circuit 613. In some embodiments, the input-switchable potential-measuring or -applying device 635 allows for addressable measurement and/or application of potential between any or every pair of electrodes 619 and 631. In some embodiments, the potential is measured. In some embodiments, the potential is applied such that the difference in voltage between electrode 619 and electrode 631 is positive. In some embodiments, the potential is applied such that the difference in voltage between electrode 619 and electrode 631 is negative. The applied potential, if any, may range in amplitude from zero to about 50 volts; or from zero to about 5 volts; or from zero to about 500 millivolts; or from zero to about 50 millivolts; or from zero to about 5 millivolts.

In some embodiments, a potential is applied between the surface of the imaging integrated circuit, which forms the bottom of the chamber, and that of the inner surface of the chamber lid, which forms the top of the chamber. Such a potential allows for movement of charged particles along the current vector; this can be useful, for example, in collecting/concentrating cells or particles at the surface of the imaging integrated circuit for optimal imaging, or at the inner surface of the chamber lid for exclusion from imaging, depending on the sign of the potential and the net charge of the cell or particle. In some embodiments, applying a potential may result in immobilization of a particle or cell at either surface. See Cook, G. M. W. (1968). *Biol. Rev.* 43, 363-391; and Bayer M E, Sloyer J L Jr. (1990) *J Gen Microbiol.* 136, 867-74; both papers are incorporated here by reference. In some embodiments, the potential is applied between one surface electrode and one chamber lid electrode. In some embodiments, the potential is applied between several surface electrodes and several chamber lid electrodes. In some embodiments, the potential is applied between substantially all surface electrodes and substantially all chamber lid electrodes.

In some embodiments, applying a potential allows for selective electroporation of a cell, killing it, as in wound healing experiments, or enabling the entrance of ordinarily impermeable molecules into that cell, as in transfection to introduce DNA or other genetic material, or to introduce dyes, drugs, etc. In some embodiments, cell migration experiments are enabled by applying a gradient of potential between the surface of the imaging integrated circuit and the chamber lid that increases across the matrix of electrodes from one side of the chamber to the other. In some embodiments, the electrodes 619 and 631 are addressable from their matrix so as to allow for cell or particle selection. In some embodiments in flow, applying a potential allows for diversion of cells or particles into an upper or lower flow stream for segregation and selection of streams by charge. In some embodiments, the switchable potential-applying or potential-measuring device 635 is used to stimulate or record electrical activity in a cell or cells close to the electrodes 619, for simultaneous or near-simultaneous microscopic imaging and electrical stimulation or recording of the cells (see as an example U.S. Pat. No. 6,297,025, incorporated here by reference).

In some embodiments, a thin layer of adhesive material 617 coats the imaging integrated circuit 613. Coatings with molecules having specific affinities can be used to exclude or enrich particular cells or other specimens of interest. Such treatment could also be used, in conjunction with fluorophores 616, nanoparticles or microbeads, for binding assays. Non-selective adhesives will create an imaging "stick patch" that could be used, as an example, for forensic applications. In some embodiments, a thin layer of light-transmissive material 614 containing fluorophores, phosphors or up-converters coats the photosensitive surface. Such molecules are excited at one wavelength and emit at another. In some embodiments, fluorophores are excited with wavelengths outside the spectrally sensitive range of the imaging integrated circuit and emitting, including by frequency upconversion, within the circuit's spectral range, thereby extending the useful spectral range of the imaging integrated circuit, e.g. into the X-ray spectrum for X-ray microscopy.

In some embodiments, the device further comprises a system for detecting Raman scattering. In some embodiments, the device further comprises a system for detecting X-ray fluorescence.

In some embodiments, an imaging device is used in conjunction with an atomic force microscope (AFM) cantilever arm 801 by placement of the imaging integrated circuit pixel (s) 805 underneath the tip of the AFM 803 (for example, see FIG. 16). Images generated by the device and the AFM are correlated. In some embodiments having a thin layer of surface plasmon generating material 619, an imaging device is used in conjunction with a surface plasmon resonance apparatus and images generated by the device and the apparatus are correlated.

Example 1

A specimen of a thin Mylar sheet was placed in direct contact with the exposed surface of a commercially available, 1.3 megapixel CMOS imaging integrated circuit having 5.2 μm×5.2 μm pixels, and an image (FIG. 11) was collected using a diffuse white light source, a computer, and commercially available image acquisition software. The upper left and upper right corners of the field of view are empty, with the specimen filling the rest of the field of view; scratches and other features of the specimen as small as single pixels are clearly visible.

Example 2

Using the CMOS imaging integrated circuit and light source of Example 1, a specimen of aerosol organic solvent was nebulized and thereby deposited onto the chip surface. Acquisition of the image produced FIG. 12.

Example 3

A 1 μl droplet of water was deposited directly onto the CMOS chip surface as in Examples 1 and 2, using the same light source. Edges of the droplet spontaneously aligned with the pixel rows and columns, yielding the unusual lozenge shape. Suspended in the droplet were Sephadex beads of sizes ranging from <20 μm to >100 μm. Acquisition of the image produced FIG. 13. The larger beads cast a prominent diffuse shadow because their equators are far from the surface. This effect would be slightly reduced with collimated illumination and is much reduced with smaller beads.

Example 4

The protective window of an Aptina CMOS imaging integrated circuit was removed, exposing the photosensitive surface of the array having of 2.2 μm×2.2 μm pixels. A diffuse white light source was used, as was a computer-based system equipped with commercially available software for image acquisition as supplied with the array. A minute sample (~100) of blood was obtained from an African clawed frog (*Xenopus laevis*) and diluted in calcium-free amphibian Ringer's solution. A drop of the diluted blood was deposited directly onto the surface of the array. Acquisition of an image by the array produced FIG. 14 (top); a small portion of this large (3.2×2.4 mm) field of view can be seen at higher magnification simply by "zooming in" on the acquired image (FIG. 9, bottom). The elliptical shape and nucleated structure of these living, unstained erythrocytes (long axis ~24 μm, short axis ~16 μm) is clearly evident. The zoomed image was enhanced by 2×2 pixel augmentation with bicubic interpolation. The images produced were intrinsically calibrated, as the dimensions of the pixels are known. In this Example, pixels are 2.2 μm wide in the raw image, and 1.1 μm wide in the 2×2 interpolated image.

Example 5

Using the same imaging integrated circuit of Example 4, a video sequence of a live *Daphnia* in pond water was obtained, a region of interest from two frames of which is shown in FIG. 15.

Other embodiments are also within the scope of the following claims.

The invention claimed is:

1. An apparatus comprising:
a portable housing comprising:
an imaging integrated circuit comprising
a two-dimensional array of pixels at a photosensitive surface to capture a two-dimensional image of a specimen, the width of the pixels along each of the two dimensions of the array being 5 microns or smaller, the array having at least 1 million pixels,
the surface to receive at least a part of a specimen at a distance from the surface equivalent to less than about half of an average size of the pixels,
the pixels situated within the array to generate signals that capture a two-dimensional image of the specimen that extends along each of the two dimensions of the array,
a chamber for the specimen, the chamber being defined partly by a chamber lid comprising a top, spaced apart from the surface by a distance less than 1 millimeter, to transmit light to illuminate the specimen,
the chamber lid being movable to permit a liquid specimen to be applied to the surface, or the chamber lid comprising a fluid channel to carry a fluid specimen into the chamber and in contact with the surface, or both,
the specimen to be held statically after being applied to the surface or carried into the chamber, or the two-dimensional image being captured at once as the fluid specimen flows past the surface,
electronics comprising a circuit board coupled to the imaging integrated circuit, and
a computing device to analyze information representing, or to display, the two-dimensional image of the specimen captured by the array, or both.

2. The apparatus of claim 1 also comprising a fluid channel to carry the specimen out of the chamber.

3. The apparatus of claim 2 also comprising one or more chamber lid electrodes contacting the top of the specimen chamber.

4. The apparatus of claim 3 in which the surface has a conductive layer functioning as one or more surface electrodes.

5. The apparatus of claim 4 also comprising wires electrically connecting the one or more surface electrodes and the one or more chamber lid electrodes to a potential-applying device.

6. The apparatus of claim 5 also comprising wires electrically connecting the one or more surface electrodes and the one or more chamber lid electrodes to a potential-measuring device.

7. The apparatus of claim 5 in which the potential-applying device is also capable of measuring a potential.

8. The apparatus of claim 5 in which the one or more chamber lid electrodes are arranged in a matrix and the potential-applying device is configured to address the one or more chamber lid electrodes individually or as a group.

9. The apparatus of claim 5 in which the one or more surface electrodes are arranged in a matrix and the potential-applying device is configured to address the one or more surface electrodes individually or as a group.

10. The apparatus of claim 1 comprising a light source to emit light primarily in the ultraviolet wavelength band and in which longer-wavelength fluorescence or phosphorescence of the specimen produces a signal.

11. A method of fluorescence lifetime imaging comprising operating the apparatus of claim 10.

12. A method of collecting specimen comprising operating the apparatus of claim 5 with a potential applied between the chamber lid electrode and the surface electrode.

13. A method of performing wound healing experiments comprising operating the apparatus of claim 5.

14. The apparatus of claim 1 in which the specimen is suspended in a fluid.

15. The apparatus of claim 1 comprising a collimated light source.

16. The apparatus of claim 1 comprising a layer attached to the surface of the array of photosensitive elements.

17. The portable apparatus of claim 1 in which the array has at least a million light-sensitive elements.

18. The portable apparatus of claim 1 comprising a pump for causing the specimen to flow through the chamber and the channel.

* * * * *